US011661583B2

(12) United States Patent
Childers et al.

(10) Patent No.: US 11,661,583 B2
(45) Date of Patent: May 30, 2023

(54) DRUG DISCOVERY PLATFORM FOR DUCHENNE CARDIOMYOPATHY

(71) Applicant: University of Washington, Seattle, WA (US)

(72) Inventors: Martin K. Childers, Seattle, WA (US); Xuan Guan, Seattle, WA (US)

(73) Assignee: University of Washington, Seattle, WA (US)

( * ) Notice: Subject to any disclaimer, the term of this patent is extended or adjusted under 35 U.S.C. 154(b) by 359 days.

(21) Appl. No.: 15/755,418

(22) PCT Filed: Aug. 25, 2016

(86) PCT No.: PCT/US2016/048671
§ 371 (c)(1),
(2) Date: Feb. 26, 2018

(87) PCT Pub. No.: WO2017/035342
PCT Pub. Date: Mar. 2, 2017

(65) Prior Publication Data
US 2020/0017833 A1 Jan. 16, 2020

Related U.S. Application Data

(60) Provisional application No. 62/210,683, filed on Aug. 27, 2015.

(51) Int. Cl.
*C12N 5/077* (2010.01)
*G01N 33/50* (2006.01)

(52) U.S. Cl.
CPC ....... *C12N 5/0657* (2013.01); *G01N 33/5044* (2013.01); *C12N 2506/45* (2013.01); *C12N 2510/00* (2013.01); *G01N 2500/10* (2013.01)

(58) Field of Classification Search
CPC .......................... C12N 5/0657; C12N 2506/45
See application file for complete search history.

(56) References Cited

U.S. PATENT DOCUMENTS

| 2010/0168072 A1 | 7/2010 | Wynne et al. |
| 2014/0140969 A1 | 5/2014 | Beausejour et al. |
| 2014/0223589 A1 | 8/2014 | Rogers et al. |
| 2014/0281573 A1 | 9/2014 | Brandan et al. |

FOREIGN PATENT DOCUMENTS

| WO | 2005053601 | 6/2005 |
| WO | 2012098260 | 7/2012 |
| WO | 2014197748 | 12/2014 |

OTHER PUBLICATIONS

Guan (Thesis. Modeling Heart Disease of Patients with Muscular Dystrophy using Induced Pluripotent Stem Cells, 1-176, Aug. 2015). (Year: 2015).*
Guan (Stem Cell Research. 12:467-480, 2014, published on line Dec. 13, 2013) (Year: 2013).*
Lin (Disease Models & Mechanisms, 8: 457-488, 2015, May 1, 2015), (Year: 2015).*
Jang (Experimental and Molecular Medicine, 44(3): 202-213, 2012). (Year: 2012).*
Dutta (J Physiol, (559(3): 799-822, 2004, (Year: 2004).*
Doss (Cells, 8(403): 1-16, 2019) (Year: 2019).*
Batalov and Feinberg (Biomarker Insights, 10(S1): 71-76, 2015) (Year: 2015).*
Guan (Stem Cell Research, 12:467-480, 2014, published on line Dec. 13, 2013) (Year: 2014).*
Araki (BBRC, 238(2): 492-497, 1997) (Year: 1997).*
Doherty (Toxicology and Applied Pharmacology, 285: 51-60, Apr. 2, 2015). (Year: 2015).*
International Preliminary Report on Patentability dated Feb. 27, 2018 for international application PCT/US16/048671.
International Search Report and Written Opinion dated Feb. 21, 2017 for international application PCT/US2016/048671.
Bostick, et al., "AAV Micro-Dystrophin Gene Therapy Alleviates Stress-Induced Cardiac Death but not Myocardial Fibrosis in >21-m-old mdx Mice, an End-Stage Model of Duchenne Muscular Dystrophy Cardiomyopathy", J Mol Cell Cardiol.. vol. 53 No. 2, Aug. 2012, 217-222.
Cong, et al., "Multiplex Genome Engineering using CRISPR/Cas Systems", Science, vol. 339 No. 6121, 2013, 819-823.
Doherty, et al., "Structural and Functional Screening in Human Induced-Pluripotent Stem Cell-Derived Cardiomyocytes Accurately Identifies Cardiotoxicity of Multiple Drug Types", Toxicology and Applied Pharmacology, vol. 285, 2015, 51-60.
Dutta, et al., "Role of ATP-Conductive Anion Channel in ATP Release from Neonatal Rat Cardiomyocytes in Ischemic or Hypoxic Conditions", The Journal of Physiology, Jul. 22, 2004, vol. 559.3, pp. 799-812, abstract figure.
Ebert, et al., "Induced Pluripotent Stem Cells as a Disease Modeling and Drug Screening Platform", Cardiovasc Pharmacol, vol. 60 No. 4, Oct. 2012.
Filareto, et al., "An Ex Vivo Gene Therapy Approach to Treat Muscular Dystrophy Using Inducible Pluripotent Stem Cells", Nature Communications, vol. 4, 2013, 1549.
Guan, et al., "Dystrophin-Deficient Cardiomyocytes Derived from Human Urine: New Biologic Reagents for Drug Discovery", Stem Cell Research, vol. 12, 2014, 467-480.

(Continued)

*Primary Examiner* — Laura Schuberg
(74) *Attorney, Agent, or Firm* — Nixon Peabody LLP; Mark J. FitzGerald

(57) ABSTRACT

Methods of screening agents in a cardiomyocyte population are provided. The cardiomyocyte population may be differentiated from a dystrophin knockout iPSC line. High-throughput methods of screening agents in a cardiomyocyte population that has been differentiated from a dystrophin knockout iPSC line are also provided. The methods may include determining an effect of the agents on membrane barrier function by using a cell viability assay. Methods of making dystrophin knockout iPSC lines, making dystrophin knockout iPSC derived cardiomyocytes, and modeling dystrophin deficient cardiomyopathy are also provided.

11 Claims, 15 Drawing Sheets

Specification includes a Sequence Listing.

(56) References Cited

OTHER PUBLICATIONS

Guan, "Modeling Heart Disease of Patients with Muscular Dystrophy using Induced Pluripotent Stem Cells (online)", Wake Forrest University Graduate School of Arts and Sciences, Aug. 2015 (retrieved on Nov. 2, 2016) retrieved from the internet: URL: http://wakespace.lib.wfu.edu/bitstream/handle/10339/57259/Guan_wfu_0248D_10793.pdf.html, pp. 1-176.
Guan, "Oral Defense of Guan Doctoral Thesis", Wake Forrest University Integrative Physiology & Pharmacology Ph. D. Program Calendar, Jul. 23, 2015, Internet Archive retrieved on Nov. 3, 2016, retrieved from the internet: URL https://web.archive.org/web/20150801102923/http://ipp.graduate.wfu.edu/calendar.
Guan, et al., "Use of Adeno-Associated Virus to Enrich Cardiomyocytes Derived from Human Stem Cells", Human Gene Therapy Clinical Development, vol. 26 No. 3, 2015.
Hoekstra, et al., "Induced Pluripotent Stem Cell Derived Cardopmyocytes as Models for Cardiac Arrhythmias", Frontiers in Physiology; vol. 3 Article 346, Aug. 2012.
Hongmei, et al., "Precise Correction of the Dystrophin Gene in Duchenne Muscular Dystrophy Patient Induced Pluripotent Stem Cells by TALEN and CRISPER-Cas9", Stem Cell Reports, vol. 4, Jan. 13, 2015, 143-154.
Idone, et al., "Repair of Injured Plasma Membrane by Rapid Ca2+-Dependent Endocytosis", The Journal of Cell Biology, vol. 180 No. 5, Mar. 10, 2008, 905-914.
Jang, et al., "Disease-Specific Induced Pluripotent Stem Cells: A Platform for Human Disease Modeling and Drug Discovery", Experimental and Molecular Medicine, vol. 44 No. 3, Mar. 2012, 202-213.
Kotini, et al., "Functional Analysis of a Chromosomal Deletion Associated with Myelodysplastic Syndromes using Isogenic Human Induced Pluripotent Stem Cells", Nature Biotechnology, vol. 33 No 6, Jun. 2015.
Lamar, et al., "Genetic Modifiers for Neuromuscular Diseases", Journal of Neuromuscular Diseases, vol. 1, 2014, 3-13.
Lian, et al., "Robust Cardiomyocyte Differentiation from Human Pluripotent Stem Cells via Temporal Modulation of Canonical Wnt Signaling", PNAS, Published on-line at www.pnas.org/cgi/doi/10.1073/pnas.1200250109. May 29, 2012.
Lin, et al., "Modeling and Study of the Mechanism of Dilated Cardiomyopathy Using Induced Pluripotent Stem Cells Derived from Individials with Duchenne Muscular Dystrophy", Disease Models & Mechanisms, vol. 8, 2015, 457-466.
Long, et al., "Prevention of muscular dystrophy in mice by CRISPR/Cas9-mediated editing of germline DNA", Science, vol. 345, 2014, 1184-1188.
Mack, et al., "Disease-in-a-Dish: the Contribution of Patient-Specific Induced Pluripotent Stem Cell Technology to Regenerative Rehabilitation", American Journal of Physical Medicine & Rehabilitation, Nov. 2014, vol. 93 (11 Suppl 3), pp. S155-S168.
Martinez, et al., "Genome Engineering of Isogenic Human ES Cells to Model Autism Disorders", Nucleic Acids Research, vol. 43 No. 10, 2015.
Merkle, et al., "Mideling Human Disease with Pluripotent Stem Cells: From Genome Association to Function", Cell Stem Cell, vol. 12, Jun. 6, 2013.
Muntoni, et al., "Dystrophin and Mutations: One Gene, Several Proteins, Multiple Phenotypes", The Lancet Neurology, vol. 2, Dec. 2003.
Murray, et al., "Brief Report: Isogenic Induced Pluripotent Stem Cell Lines from an Adult with Mosaic Down Syndrome Midel Accelerated Neuronal Ageing and Neurodegeneration", Stem Cells, vol. 33, 2015, 2077-2084.
Nakamura, et al., "Generation of Muscular Dystrophy Model Rats with a CRISPR/Cas System", Scientific Reports, vol. 4 No. 5635, 2014.
Navarrete, et al., "Screening Drug-Induced Arrhythmia Using Human Induced Pluripotent Stem Cell-Derived Cardiomyocytes and Low-Impedance Microelectrode Arrays", Department of Medicine, Division of Cardiology, Stanford University School of Medicine—Presented at the 2012 American Heart Association meeting in Los Angeles, CA, Nov. 3-7, 2012.
Ng, et al., "Human Long Non-Coding RNAs Promote Pluripotency and Neuronal Differentiation by Association with Chromatin Modifiers and Transcription Factors", The EMBO Journal, vol. 31 No. 3, 2012.
Ousterout, et al., "Multiplex CRISPR/Cas9-Based Genome Editing for Correction of Systrophim Mutations That Cause Duchenne Muscular Dystrophy", Nature Communications, vol. 6 No. 6244, Feb. 18, 2015.
Pravdic, et al., "Anesthetic-Induced Preconditioning Delays Opening of Mitochondrial Permeability Transition Pore via Protein Kinase C-ε Mediated Pathway", Anesthesiology vol. 111 No. 2, Aug. 2009, 267-74.
Ran, et al., "Genome Engineering Using the CRISPR-Cas9 System", Nature Protocols, vol. 8 No. 11, 2013.
Ryan, et al., "Isogenic Human iPSC Parkinson's Model Shows Nitrosative Stress-Induced Dysfunction in MEF2-PGC1α Transcription", NIH Public Access, Author Manuscript; Cell, Dec. 5, 2013.
Sadek, et al., "Cardiogenic Small Molecules that Enhance Myocardial Repair by Stem Cells", PNAS, vol. 105 No. 16, Apr. 22, 2008, 6063-6068.
Schneider, et al., "NIH Image to InageJ: 25 Years of Image Analysis", Author Manuscript, Available in PMC, Nat Methods, vol. 9 No. 7, Jul. 2012, 671-675.
Shaltouki, et al., "Mitochondrial Alterations by PARKIN in Dopaminergic Neurons Using PARK2 Patient-Specific and PARK2 Knockout Isogenic iPSC Lines", Stem Cell Reports, vol. 4, May 12, 2015, 847-859.
Soldner, et al., "Generation of Isogenic Pluripotent Stem Cells Differing Exclusively at Two Early Onset Parkinson Point Mutations", Cell, vol. 146, Jul. 22, 2011, 318-331.
Talbert, et al., "A Multi-Parameter In Vitro Screen in Human Stem Cell-Derived Cardiomyocytes Identifies Ponatinib-Induced Structural and Functional Cardiac Toxicity", Society of Toxicology Toxicological Sciences, vol. 143 No. 1, 2015, 147-155.
Wang, et al., "Modeling the Mitochondrial Cardiomyopathy of Barth Syndrome with Induced Pluripotent Stem Cell and Heart-On-Chip Technologies", Nature Medicine, vol. 20, No. 6, Jun. 2014, 616-623.
Wen, et al., "Synaptic Dysregulation in a Human iPS Cell Model of Mental Disorders", Nature, vol. 515, Nov. 20, 2014.
Willems, et al., "Small Molecule-Medicated TGF-β Type II Receptor Degradation Pormotes Cardiomyogenesis in Embryonic Stem Cells", Cell Stem Cell, vol. 11, Aug. 3, 2012, 242-252.
Willems, et al., "Small-Molecule Inhibitors of the Wnt Pathway Potently Promote Cardiomyocytes from Human Embryonic Stem Cell-Derived Mesoderm", American Heart Association Inc., Circulation Research available at http://circres.ahajournals.org, 2011.

\* cited by examiner

Oct4 SSEA4 Nuclei          Tra1-60 Sox2 Nuclei

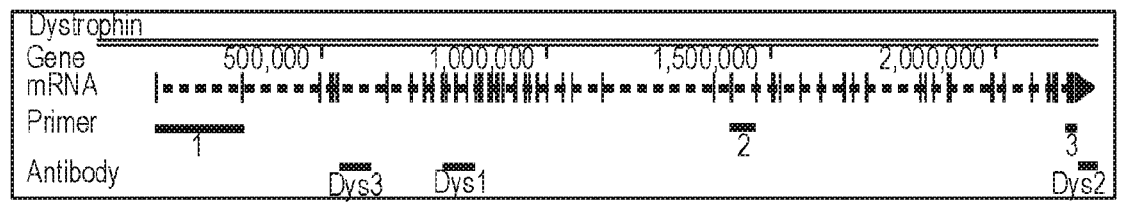
FIG. 2A
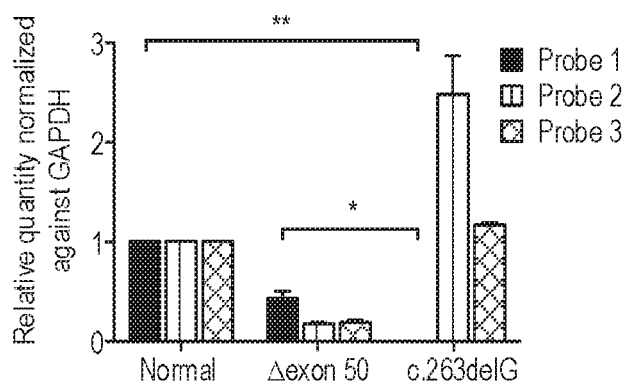
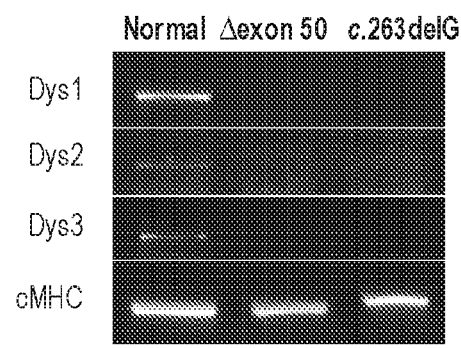
FIG. 2B
FIG. 2C

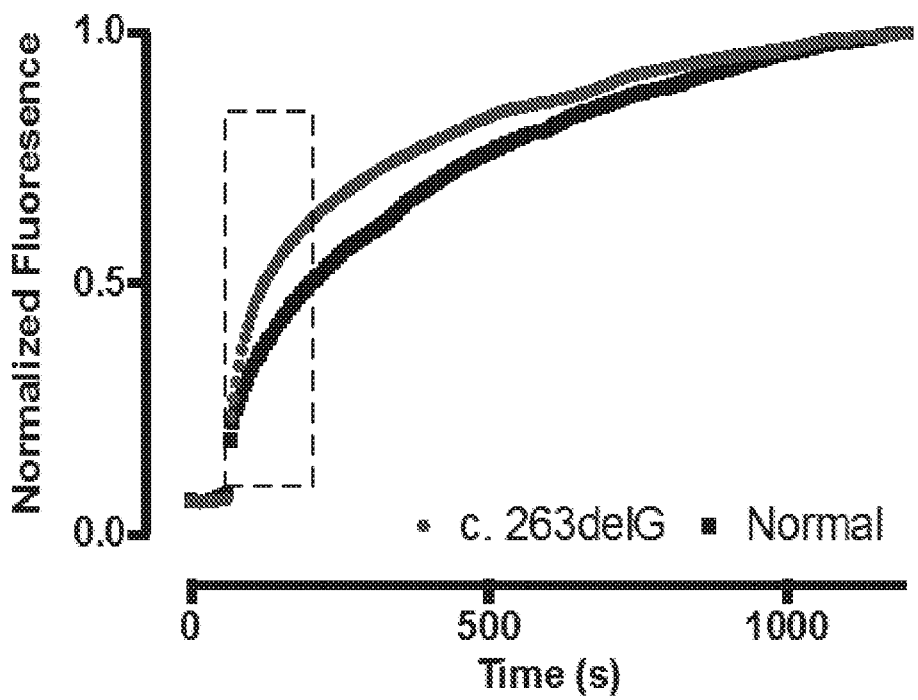
FIG. 5C
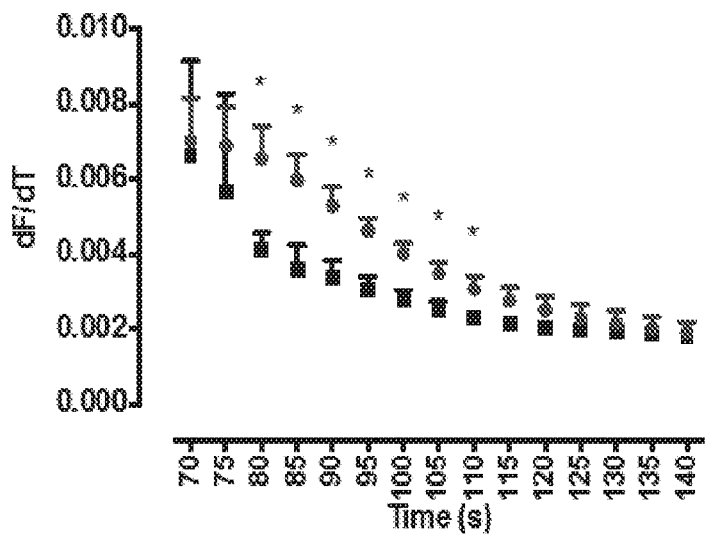 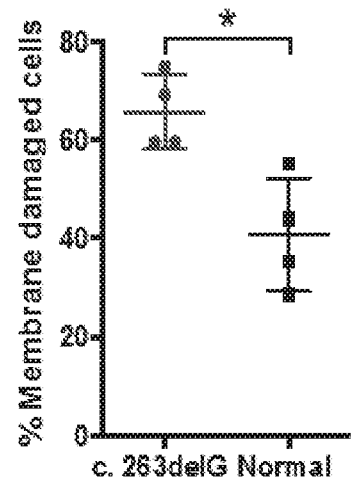
FIG. 5D          FIG. 5E

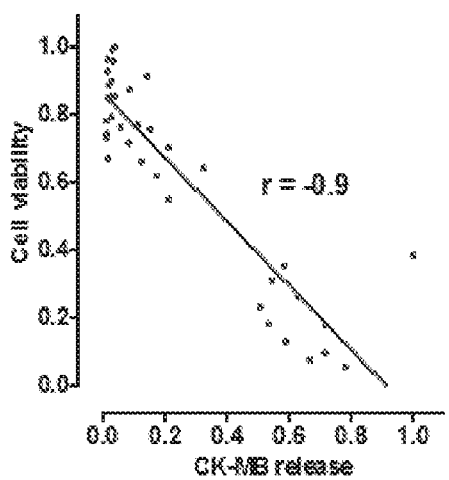
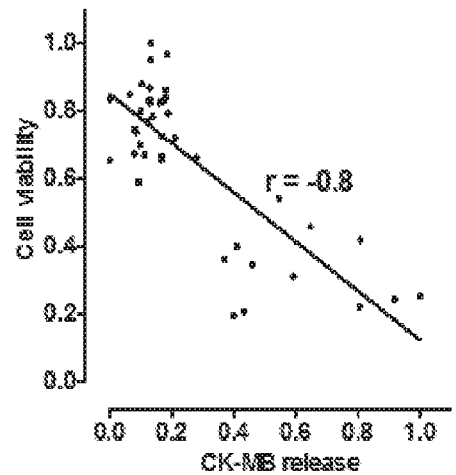
FIG. 6A  FIG. 6B
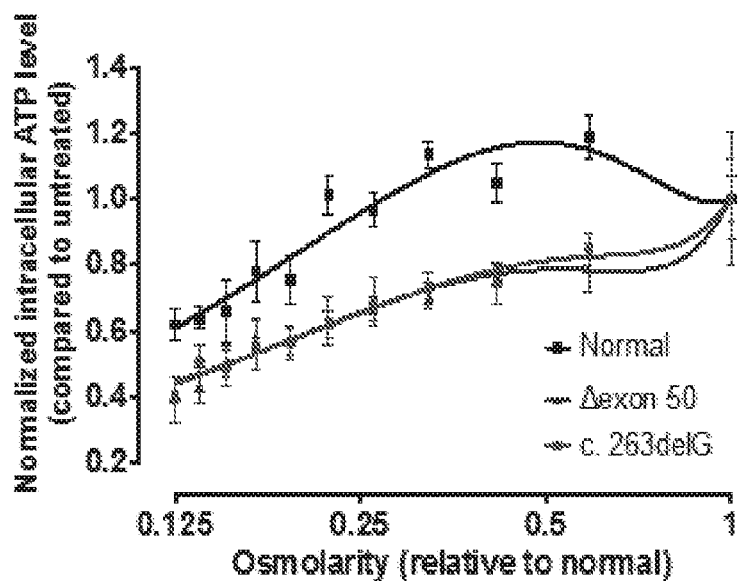
FIG. 6C

%indel 40.7 41.8 35.4 44.3

SEQUENCE LISTING

```
<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: Wild-type dystrophin exon 1 guide RNA

<400> SEQUENCE: 1
atgctttggt gggaagaagt agagga                                              26

<210> SEQ ID NO 2
<211> LENGTH: 26
<212> TYPE: DNA
<213> ORGANISM: Artificial Sequence
<220> FEATURE:
<223> OTHER INFORMATION: c.263delG modified dystrophin exon 1 guide RNA

<400> SEQUENCE: 2
atgctttggt gggaagaata gaggac                                              26

<210> SEQ ID NO 3
<211> LENGTH: 38
<212> TYPE: DNA
<213> ORGANISM: Artificial Sequence
<220> FEATURE:
<223> OTHER INFORMATION: Primer DMD-F

<400> SEQUENCE: 3
tgtaaaacga cggccagtgg cctctacaga atcctggc                                 38

<210> SEQ ID NO 4
<211> LENGTH: 37
<212> TYPE: DNA
<213> ORGANISM: Artificial Sequence
<220> FEATURE:
<223> OTHER INFORMATION: Primer DMD-R

<400> SEQUENCE: 4
caggaaacag ctatgacagg cctccatgta gttccta                                  37

<210> SEQ ID NO 5
<211> LENGTH: 23
<212> TYPE: DNA
<213> ORGANISM: Artificial Sequence
<220> FEATURE:
<223> OTHER INFORMATION: Guide 1

<400> SEQUENCE: 5
ttgtgacaag ctcactaatt agg                                                 23
```

```
<210> SEQ ID NO 6
<211> LENGTH: 23
<212> TYPE: DNA
<213> ORGANISM: Artificial Sequence
<220> FEATURE:
<223> OTHER INFORMATION: Guide 2

<400> SEQUENCE: 6
aagtttgaag aactttttacc agg                                              23

<210> SEQ ID NO 7
<211> LENGTH: 23
<212> TYPE: DNA
<213> ORGANISM: Artificial Sequence
<220> FEATURE:
<223> OTHER INFORMATION: Guide 3

<400> SEQUENCE: 7
aggcagcgat aaaaaaaacc tgg                                               23

<210> SEQ ID NO 8
<211> LENGTH: 23
<212> TYPE: DNA
<213> ORGANISM: Artificial Sequence
<220> FEATURE:
<223> OTHER INFORMATION: Guide 4

<400> SEQUENCE: 8
gctttggtgg gaagaagtag agg                                               23

<210> SEQ ID NO 9
<211> LENGTH: 41
<212> TYPE: DNA
<213> ORGANISM: Homo sapiens

<400> SEQUENCE: 9
aaaatgcttt ggtgggaaga agtagaggac tgttgtaagt a                           41
```

DRUG DISCOVERY PLATFORM FOR DUCHENNE CARDIOMYOPATHY

CROSS-REFERENCE TO RELATED APPLICATIONS

This application is a 35 U.S.C. § 371 National Phase Entry Application of International Application No. PCT/US2016/048671, filed Aug. 25, 2016, which designates the U.S., and claims the benefit of U.S. Provisional Application No. 62/210,683, filed Aug. 27, 2015, which are incorporated by reference in their entireties.

SEQUENCE LISTING

The sequence listing of the present application has been submitted electronically via EFS-Web as an ASCII formatted sequence listing with a file name "SequenceListing_UW1301.txt", creation date of Sep. 2, 2016 and a size of 1,855 bytes. The sequence listing submitted via EFS-Web is part of the specification and is herein incorporated by reference in its entirety.

TECHNICAL FIELD

The present disclosure relates generally to methods of screening agents in a cardiomyocyte population. In particular, the methods may relate to determining an effect of an agent on one or more phenotypes in a cardiomyocyte population differentiated from a dystrophin knockout induced pluripotent stem cell (iPSC) line. In particular, the phenotype may be membrane barrier function. The present disclosure also relates to methods of making dystrophin knockout iPSC lines and methods of making dystrophin knockout iPSC derived cardiomyocytes. In particular, methods of making dystrophin knockout iPSC derived cardiomyocytes may include differentiating a dystrophin knockout iPSC line.

BACKGROUND

Mutation of the dystrophin gene is the molecular basis of Duchenne muscular dystrophy (DMD) and its milder variant, Becker's muscular dystrophy (BMD), one of the most common fatal genetic disorders, affecting 1 in 3,500 boys. Cardiac abnormalities are generally associated with DMD and BMD patients, and it has been shown that about half of DMD and BMD patients eventually succumb to cardiac failure.

Previous studies with animal models have uncovered several cellular events associated with the absence of dystrophin. Without being bound by any particular theory, a decrease of membrane barrier function may be the primary defect associated with the absence of dystrophin, i.e., as a result of a disintegrated dystroglycan complex. Abnormal membrane function impairs calcium handling and mitochondria function, opening mitochondria permeability transition pore (mPTP) to initiate apoptosis. Unfortunately, animal disease models, especially mdx mouse, differ considerably from human patients in both physiology and pathogenesis. Thus, for certain applications such as drug discovery, cell-based studies on human tissue could potentially provide a better translational context.

The advent of human induced pluripotent stem cell (iPSC) technology may provide an opportunity to study early cellular events on a patient's own cells. Recently, DMD iPSCs with various dystrophin mutations have been generated (see Li, H. L. et al., *Stem Cell Reports* (2014); Lin, B. et al., *Dis Model Mech* (2015); and Guan, X. et al., *Stem Cell Res* 12, 467-480 (2014)). Data has shown that cardiomyocytes derived from such iPSCs may reproduce several key features of the disease, including elevated resting intracellular calcium level, mitochondria abnormality, and activated apoptotic pathway (see Lin, B. et al., *Dis Model Mech* (2015)). These results may indicate the feasibility of using iPSCs to model dystrophin deficient cardiomyopathy. However, the lack of a genetically matched control in these studies may make it difficult to attribute the observed phenotypic difference(s) solely to the disease-causing mutation, as differences in genetic background can modify delicate cellular phenotypes (see Hoekstra, M., et al., *Frontiers in physiology* 3, 346 (2012)).

The technology advancement in genome editing has simplified eukaryotic genome modification. Consequently, isogenic iPSC pairs that only differ in disease-causing mutations (see Soldner, F. et al., *Cell* 146, 318-331 (2011); Ryan, S. D. et al., *Cell* 155, 1351-1364 (2013); Wang, G. et al., *Nat Med* 20, 616-623 (2014); Shaltouki, A. et al., *Stem Cell Reports* (2015); Martinez, R. A. et al., *Nucleic Acids Res* (2015); Murray, A. et al., *Stem Cells* (2015); Wen, Z. et al., *Nature* 515, 414-418 (2014); and Kotini, A. G. et al., *Nat Biotechnol* (2015)), including dystrophin (see Li, H. L. et al., *Stem Cell Reports* (2014)), have been created by targeting genomes with zinc finger nuclease, CRISPR-Cas9 enzyme, or TALEN nuclease. These isogenic pairs can be useful for studying the effect of a certain genetic variant and/or minimizing the impact of underlying genetic background noise.

BRIEF DESCRIPTION OF THE DRAWINGS

The embodiments disclosed herein will become more fully apparent from the following description and appended claims, taken in conjunction with the accompanying drawings.

FIG. 2A is a schematic representation of the relative positions of PCR probes and antibodies epitopes in the dystrophin gene and mRNA.

FIG. 2B is a graph of quantitative RT-PCR demonstrating a normal control, a DMD patient (Δexon 50), and CRISPR modified (c.263delG) human cardiomyocytes, assayed with various dystrophin probes. Data indicate the complete absence of dystrophin transcript detected by probe 1 (black bar). All values are normalized against housekeeping gene, GAPDH, and compared to a normal control.

FIG. 2C is an immunoblot against dystrophin. As shown, using various anti-dystrophin antibodies (Dys1, Dys2, and Dys3) fails to detect dystrophin in both patient and CRISPR-modified lines (Δexon 50 and c.263delG respectively). cMHC was included as a loading control.

FIGS. 5A and 5B depict that cardiomyocyte CKMB release is elicited by hypotonic solutions, 12.5%, 25%, 50%, and 100% of normal. Values are normalized against total CKMB content in cell lysate.

FIG. 5C is a graph depicting FM 1-43 fluorescence intensity in 20% hypotonic solution, normalized by the final image. The region in the dashed box is highlighted in FIG. 5D.

FIG. 5D is a graph depicting the rate of fluorescence increase (dF/dT) from 70 s to 140 s, indicating mutant cardiomyocytes accumulate FM 1-43 dye faster from 80 s to 110 s.

FIG. 5E is a graph depicting the percentage of membrane damaged cells, identified by intracellular retention of FM 1-43, after 20 minutes of hypotonic stress, indicating hypotonic stress causes greater damage in mutant cardiomyocytes.

FIG. 6A is a graph depicting a correlation of normalized cell viability and normalized CKMB release of mutant cardiomyocytes (c.263delG) (r=−0.9)

FIG. 6B is a graph depicting a correlation of normalized cell viability and normalized CKMB release of normal cardiomyocytes (r=−0.8). FIGS. 6A and 6B demonstrate an inverse correlation between CKMB release and cell viability.

FIG. 6C is a graph depicting intracellular ATP content of cardiomyocytes in 384 wells treated with hypotonic solutions with various osmolarity, indicating hypotonic stress inflicted greater decrease of cell viability to patient and mutant cardiomyocytes. All data were normalized against cells in isotonic solution.

DETAILED DESCRIPTION

Figure 1A:
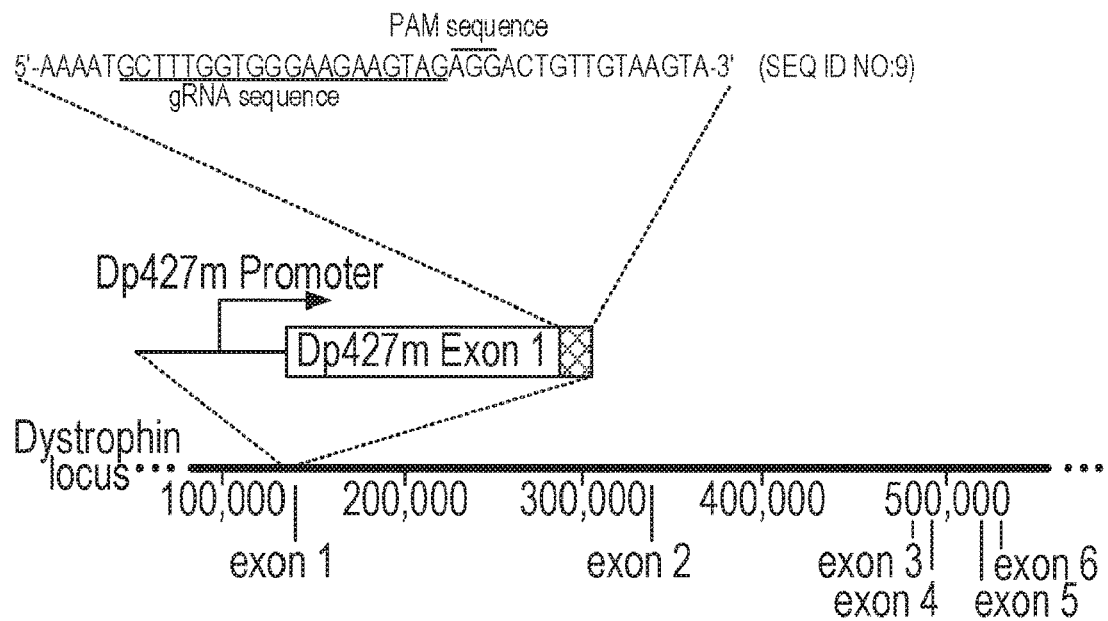
FIG. 1A depicts the use of CRISPR-Cas9 enzyme to target the dystrophin exon 1 in a normal iPSC line to create an isogenic dystrophin-modified line.

The present disclosure relates generally to methods of screening one or more agents in a cardiomyocyte population. The cardiomyocyte population may be differentiated from a dystrophin knockout iPSC line. The present disclosure also relates to high-throughput methods of screening one or more agents in a cardiomyocyte population that has been differentiated from a dystrophin knockout iPSC line. The methods may include determining an effect of the one or more agents on membrane barrier function, for example, by using a cell viability assay. Further, the present disclosure relates to methods of making dystrophin knockout iPSC lines, methods of modeling dystrophin deficient cardiomyopathy, and methods of making dystrophin knockout iPSC derived cardiomyocytes.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. Unless specifically defined otherwise, the technical terms, as used herein, have their normal meaning as understood in the art.

DMD and normal iPSC lines have been generated from human urine, and some phenotypes that may be associated with the absence of dystrophin have been identified (see Guan, X. et al., *Stem Cell Res* 12, 467-480 (2014)). The present disclosure provides the derivation of a knockout iPSC line by obliterating a dystrophin locus using the CRISPR-Cas9 enzyme. Based, at least in part, on this isogenic control, previously identified phenotypes have been evaluated. These phenotypes include membrane abnormality, calcium handling, and mitochondria permeability transition pore (mPTP) opening. In some embodiments, the decrease of membrane barrier function may be a robust disease feature of DMD. Furthermore, a membrane fragility assay has been miniaturized (as described in further detail below) to a high-throughput compatible format for semi-automated phenotypic screening. In certain embodiments, the personalized platforms disclosed herein may have utility in drug screening.

A first aspect of the disclosure relates to methods of screening one or more agents. In some embodiments, the agent may be a drug, a compound, a small molecule, a protein, a peptide, a nucleic acid, or any other suitable agent. In certain embodiments, the methods of screening the agents may include obtaining a cardiomyocyte population, wherein the cardiomyocyte population is differentiated from a dystrophin knockout iPSC line.

The methods of screening the agents may further include contacting the cardiomyocyte population with an agent. Furthermore, upon contacting the cardiomyocyte population with the agent, one or more effects of the agent on one or more phenotypes of the cardiomyocyte population may be assessed and/or determined. For example, the method may include determining one or more effects of the agent on membrane barrier function in the cardiomyocyte population. To determine one or more effects of the agent on membrane barrier function, the method of screening the agent may further include contacting the cardiomyocyte population with a hypotonic solution. In various embodiments, determining an effect of the agent on membrane barrier function in the cardiomyocyte population may include conducting a cell viability assay. Further, the cell viability assay may include quantifying ATP in the cardiomyocyte population.

In some embodiments, the cardiomyocyte population can include a deletion of guanine 263 (c.263delG) in the Dp427m dystrophin isoform. In various embodiments, the cardiomyocyte population can include one or more other suitable mutations, insertions, deletions, etc.

In certain embodiments, the cardiomyocyte population may be a mammalian cardiomyocyte population. For example, the cardiomyocyte population may be a human cardiomyocyte population. Additionally, the method of screening the agent may be a high-throughput method. A high-throughput method may include the use of one or more of robotics, data processing software, control software, liquid handling devices, and/or detectors. A high-throughput method may also allow conducting of tens, hundreds, thousands, or millions of screening tests. In some embodiments, the high-throughput method may be semi-automated or automated.

Another aspect of the disclosure relates to methods of screening an agent including obtaining a dystrophin knockout iPSC population and/or differentiating the dystrophin knockout iPSC population to form a dystrophin knockout cardiomyocyte population. The method of screening the agent may further include contacting the dystrophin knockout cardiomyocyte population with the agent and determining an effect of the agent on one or more phenotypes of the cardiomyocyte population. For example, the method may include determining an effect of the agent on membrane barrier function in the dystrophin knockout cardiomyocyte population.

As discussed above, the dystrophin knockout iPSC population may include a deletion of guanine 263 (c.263delG) in the Dp427m dystrophin isoform. In some embodiments, the dystrophin knockout iPSC population may express at least one of Oct4, SSEA4, Tra-1-60, and/or Sox2. In some other embodiments, the dystrophin knockout iPSC population may express each of Oct4, SSEA4, Tra-1-60, and Sox2.

The dystrophin knockout cardiomyocyte population can have one or more characteristics of a dystrophin deficient cardiomyopathy. For example, the dystrophin knockout cardiomyocyte population may have one or more characteristics selected from, but not limited to, a decrease of membrane barrier function (such as penetration by a dye, FM 1-43), slower calcium reuptake, expression of creatine kinase MB (CKMB), expression of troponin I, expression of troponin T, and/or susceptibility to mitochondria permeability transition pore (mPTP) opening.

In certain embodiments, the step of determining an effect of the agent on membrane barrier function in the dystrophin knockout cardiomyocyte population may comprise conducting a cell viability assay. Further, the cell viability assay may include contacting the dystrophin knockout cardiomyocyte population with a hypotonic solution. In various embodiments, the cell viability assay may comprise quantification of ATP in the dystrophin knockout cardiomyocyte population. For example, the cell viability assay may include quantifying the levels of ATP in the dystrophin knockout cardiomyocyte population.

Another aspect of the disclosure relates to recombinant or synthetic nucleic acid molecules. The wild-type dystrophin exon 1 guide RNA (gRNA) sequence is 5'-ATGCTTTGGTGGGAAGAAGTAGAGGA-3' (SEQ ID NO:1). The c.263delG modified dystrophin exon 1 gRNA sequence is 5'-ATGCTTTGGTGGGAAGAATAGAGGAC-3' (SEQ ID NO:2). In some embodiments, the recombinant or synthetic nucleic acid molecule may include at least a portion of the nucleic acid sequence of SEQ ID NO:2. For example, the recombinant or synthetic nucleic acid molecule may include all of the nucleic acid sequence of SEQ ID NO:2. In some embodiments, the nucleic acid molecule includes at least one mutation relative to the corresponding wild type sequence. In certain other embodiments, the nucleic acid molecule includes at least two, three, four, five, or more mutations relative to the corresponding wild type sequence. Also disclosed herein are plasmids including a recombinant or synthetic nucleic acid molecule including at least a portion of the nucleic acid sequence of SEQ ID NO:2.

Another aspect of the disclosure relates to one or more iPSCs including a recombinant or synthetic nucleic acid molecule including at least a portion of the nucleic acid sequence of SEQ ID NO:2. In some embodiments, the one or more iPSCs include the nucleic acid sequence of SEQ ID NO:2, wherein the nucleic acid molecule includes at least one mutation relative to the corresponding wild type sequence. In some other embodiments, the nucleic acid molecule includes at least two, three, four, five, or more mutations relative to the corresponding wild type sequence.

In certain embodiments, the one or more iPSCs have substantially normal or normal stem cell morphology. In various embodiments, the one or more iPSCs express at least one of Oct4, SSEA4, Tra-1-60, and/or Sox2. In various other embodiments, the one or more iPSCs express each of Oct4, SSEA4, Tra-1-60, and Sox2. The one or more iPSCs may also have a substantially normal or normal karyotype.

Another aspect of the present disclosure relates to methods of making a dystrophin knockout iPSC line. The methods can include transforming a plasmid including a recombinant or synthetic nucleic acid molecule including at least a portion of the nucleic acid sequence of SEQ ID NO:2 into a wild type iPSC line. The methods may also include using a CRISPR-Cas9 enzyme to target dystrophin exon 1 in the wild type iPSC line to make the dystrophin knockout iPSC line.

Another aspect of the present disclosure relates to methods of modeling dystrophin deficient cardiomyopathy. In some embodiments, the methods of modeling dystrophin deficient cardiomyopathy may include evaluating a phenotype selected from at least one of, but not limited to, membrane abnormality (such as penetration by a dye, FM 1-43), calcium handling, expression of creatine kinase MB (CKMB), expression of troponin I, expression of troponin T, and/or mitochondria permeability transition pore (mPTP) opening in a dystrophin knockout iPSC line. The dystrophin knockout iPSC line may be made as described above.

Another aspect of the present disclosure relates to methods of making dystrophin knockout iPSC derived cardiomyocytes. In certain embodiments, the methods may include differentiating a dystrophin knockout iPSC line to obtain cardiomyocytes differentiated from the dystrophin knockout iPSC line. The dystrophin knockout iPSC line may be made as described above.

In some embodiments, a phenotype-based, high-throughput screening method, as disclosed herein, can be a tool for interrogating biological systems in a substantially unbiased fashion without a pre-defined molecular target.

In contrast to traditional, target-centric assays, phenotypic screening can utilize phenotypes as its readout. Thus, selecting the "correct" phenotype can determine the downstream screening. Generally, an ideal readout phenotype sufficiently mirrors clinical presentations and recapitulates nodal points of pathogenic process, so that reversal of this abnormal trait could reliably predict in vivo efficacy. Previously, DMD patient cardiomyocytes have been characterized and it has been reported that a patient's cells can differ from normal counterparts in several aspects, including decrease of membrane barrier function, slower calcium reuptake, and susceptibility to mPTP opening (see Guan, X. et al., *Stem Cell Res* 12, 467-480 (2014)). It has been difficult, however, to definitively attribute these abnormal traits to the absence of dystrophin, due, at least in part, to phenotypic noise that can be caused by the variable genetic backgrounds of unrelated iPSC lines and that can potentially impact cellular features (see Merkle, F. T. et al., *Cell stem cell* 12, 656-668 (2013)).

As disclosed herein, a dystrophin knockout iPSC line, c.263delG, has been generated by introducing a frameshift mutation to the dystrophin locus of a male iPSC line. Cardiomyocytes differentiated from this mutant line are dystrophin negative.

To characterize mutant cardiomyocytes, three physiological assays described in a previous study were employed (see Guan, X. et al., *Stem Cell Res* 12, 467-480 (2014)). Results demonstrated that c.263delG cardiomyocytes mirrored certain aspects of DMD patient cells, manifesting prolonged calcium reuptake and impaired membrane barrier function in the face of hypotonic stress. On the other hand, the mPTP opening kinetics of the engineered mutant cells were generally comparable to the normal control. This finding may underscore an advantage of isogenic control to dissect the effect of certain mutations. Increased susceptibility of mPTP opening, however, may be a disease feature that relates to dystrophin deficiency.

The inconsistent response between patient cells and engineered mutant cells may be explained by the fact that engineered dystrophin mutation (c.263delG) is different from the mutation harbored in the patient (exon 50 deletion). Certain cellular phenotypes may be mutation specific, analogous to the varying disease severity of different mutations (see Muntoni, F. et al., *Lancet Neurol* 2, 731-740 (2003)). Also, disease symptoms can be modified by other genetic make-ups, termed disease modifiers (see Ng, S.-Y. et al. *EMBO J* 31, 522-533 (2012) and Lamar, K. M. et al., *J Neuromuscul Dis* 1, 3-13 (2014)). An alternative explanation may be that the normal iPSC line, from which the mutant was derived, may contain genetic modifiers impeding disease manifestation. In such a case, correcting the dystrophin mutation in patient iPSCs may be useful in determining the relevance of increased susceptibility of mPTP opening.

Without being bound by any particular theory, the decrease of membrane barrier function may be the most robust phenotype of dystrophin deficient cardiomyocytes. Accordingly, this assay was adapted into a high-throughput format. A useful cellular assay for phenotypic drug discovery may include a quantifiable readout with large dynamic range, as well as a straightforward procedure permitting robotic automation. Though ELISA measurement of CKMB release can robustly distinguish diseased cells from normal, it may be less amenable to screening because of its narrow dynamic range and labor-intensive assay procedure. Thus, the utility of cell viability as an assay readout was tested. Results demonstrated that hypotonicity-induced CKMB release can be inversely correlated with intracellular ATP content, suggesting the severity of membrane damage may be associated (or directly associated) with cell viability. Using cell viability as the readout, a robotic hypotonic stress assay in 384 wells clearly differentiated normal control and dystrophin deficient cells.

Figure 8:
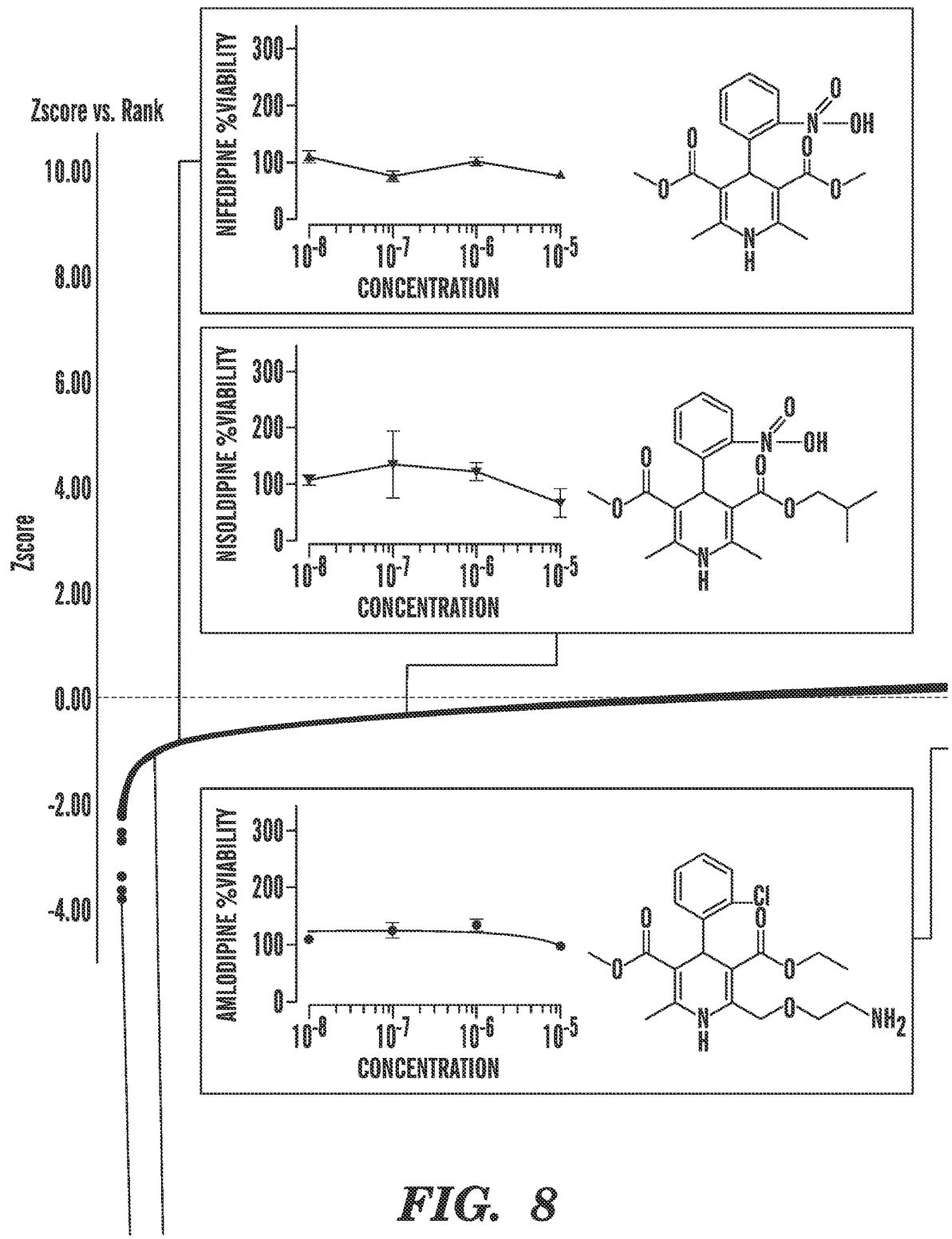
FIG. 8 is a diagram depicting representative "hit" compounds. All data points are re-ranked based on the Z score. Representative compounds are shown with dose-response curve and molecular structure.
Figure 8:
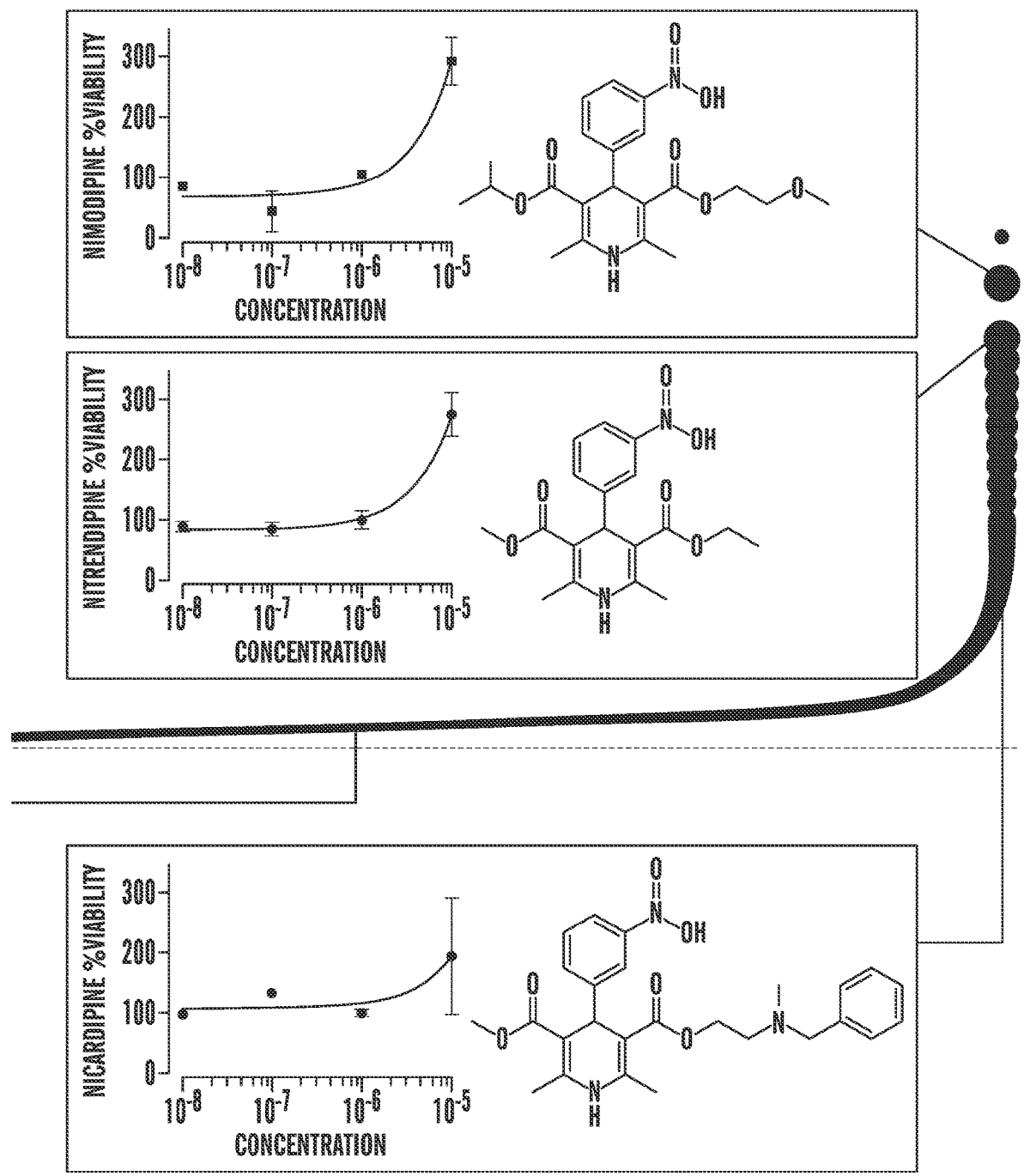
Figure 8:
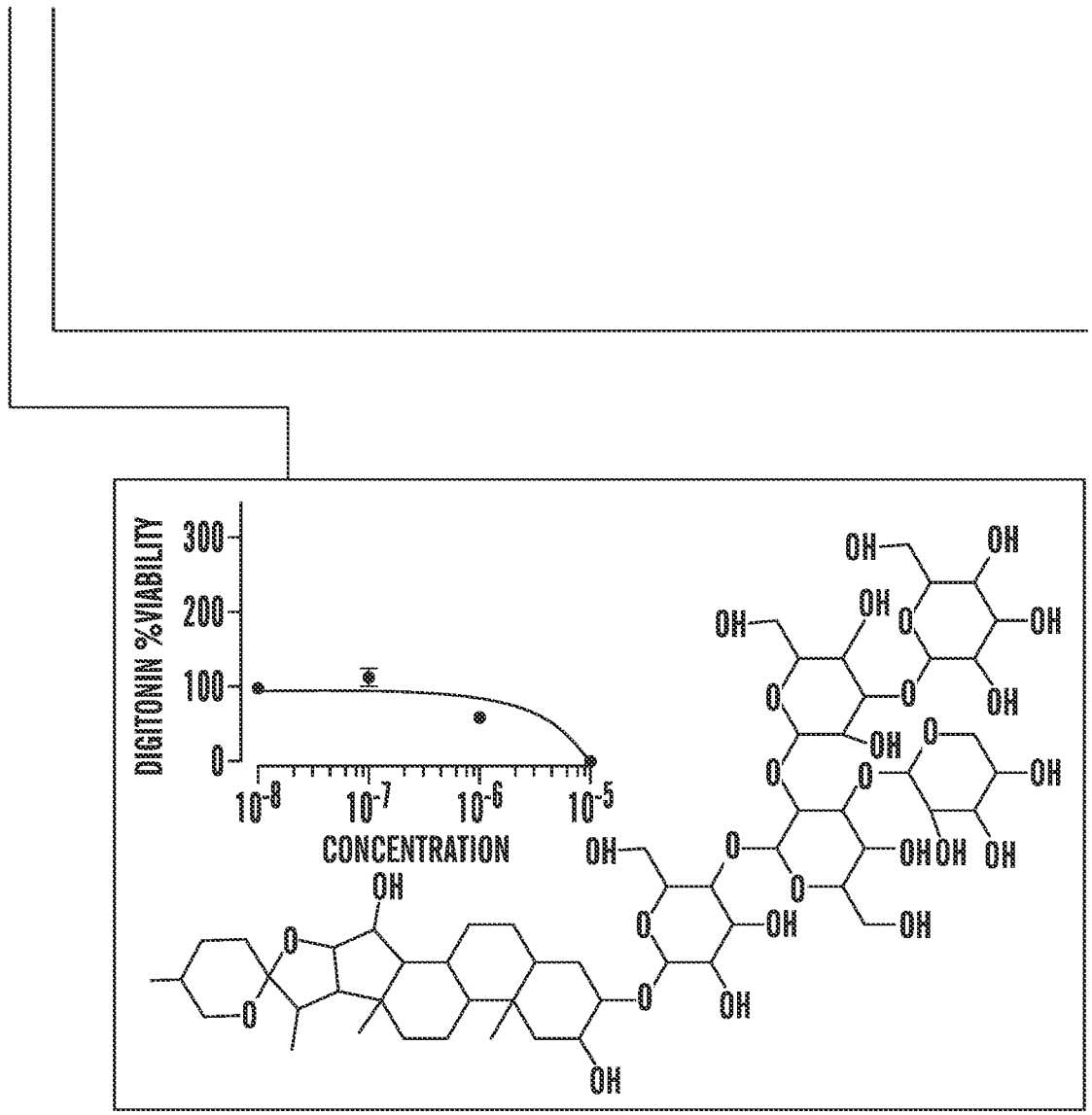
Figure 8:
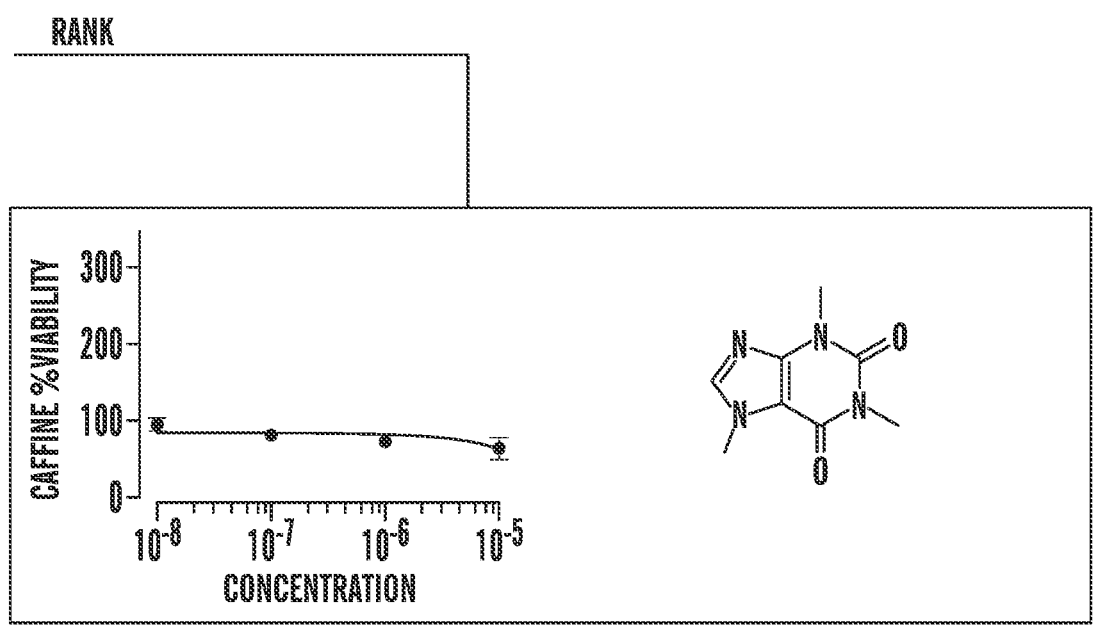

Primary screening with a library consisting of 2,000 compounds identified 39 (2%) hits with varied mechanisms of action, such as nonsteroidal anti-inflammatory drugs (NSAIDs), calcium channel blockers, antineoplastic agents, antihistamines, etc. Some hits target critical disease pathophysiological processes. For example, the permeabilizing detergent digitonin manifested a dose-responsive toxicity with the lowest Z score, possibly through aggravating membrane injury. Moreover, two calcium channel blockers, which potentially counteract the pathogenic intracellular calcium overload, were within the top candidate compounds. Caffeine, a calcium-mimetic chemical known for promoting SR calcium release, demonstrated the opposite effect. Structure-activity relationship was also evident. 3-nitrophenyl containing drugs nimodipine, nitrendipine, and nicardipine all manifested a salutary effect. Within the same class of dihydropyridine calcium channel blockers, 2-nitrophenyl containing nifedipine, nisoldipine, and 2-chlorophynyl amlodipine did not reveal a similar effect (see FIG. 8).

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—iPSC Maintenance and Cardiac Differentiation

Normal, patient (Δexon 50), and engineered dystrophin mutant (c.263delG) iPSCs were used. The derivation and maintenance of iPSCs was described previously (see Guan, X. et al., *Stem Cell Res* 12, 467-480 (2014)). Briefly, undifferentiated iPSCs were maintained in a feeder-free condition with daily change of mTeSR-1 medium (STEMCELL™ TECHNOLOGIES, Vancouver, BC, Canada) following the manufacturer's instructions. Every 4-5 days, cells were passaged by incubating with VERSENE™ Solution (LIFE TECHNOLOGIES™ Grand Island, N.Y.) for 7 minutes at room temperature and split at the ratio of 1:3-1:5. The cardiac induction method was described previously, with modification (see Lian, X. et al., *Proceedings of the National Academy of Sciences* (2012)). Briefly, after incubating with VERSENE™ Solution, iPSCs were plated in MATRIGEL™-coated (CORNING®, Tewksbury, Mass.) 24-well plates at a density of 250,000 cells/cm$^2$. Three days post seeding, cells were treated with 10 μM of CHIR-99021 (SELLECK CHEMICALS™, Houston, Tex.) for 24 hours in differentiation medium consisting of RPMI 1640 medium, 2% of B-27® minus insulin supplement, 1% L-Glutamine, and 1% of penicillin/streptomycin. All cell culture reagents are from LIFE TECHNOLOGIES™. Three days post CHIR-99021 treatment, differentiation medium was refreshed with 5 μM of IWP-4 (STEMCELLS™, Cambridge, Mass.). Two days post IWP-4 treatment, medium was switched to cardiac maintenance medium consisting of RPMI 1640 with B-27® culture supplement (LIFE TECHNOLOGIES™). Maintenance medium was replaced every other day.

Example 2—Construction of Cas9/Guide RNA Expressing Vectors

Guide sequences targeting the 3'-end of the first muscle exon of human dystrophin were designed using the online CRISPR design tool (http://crispr_mit_edu/) supported by the Zhang lab at MIT (see Cong, L. et al., *Science* 339, 819-823 (2013)). Four guide sequences with the highest score were selected:

```
Guide 1:
                                         (SEQ ID NO: 5)
TTGTGACAAGCTCACTAATTAGG;

Guide 2:
                                         (SEQ ID NO: 6)
AAGTTTGAAGAACTTTTACCAGG;

Guide 3:
                                         (SEQ ID NO: 7)
AGGCAGCGATAAAAAAAACCTGG;
and Guide 4:
                                         (SEQ ID NO: 8)
GCTTTGGTGGGAAGAAGTAGAGG.
```

Figure 9A:
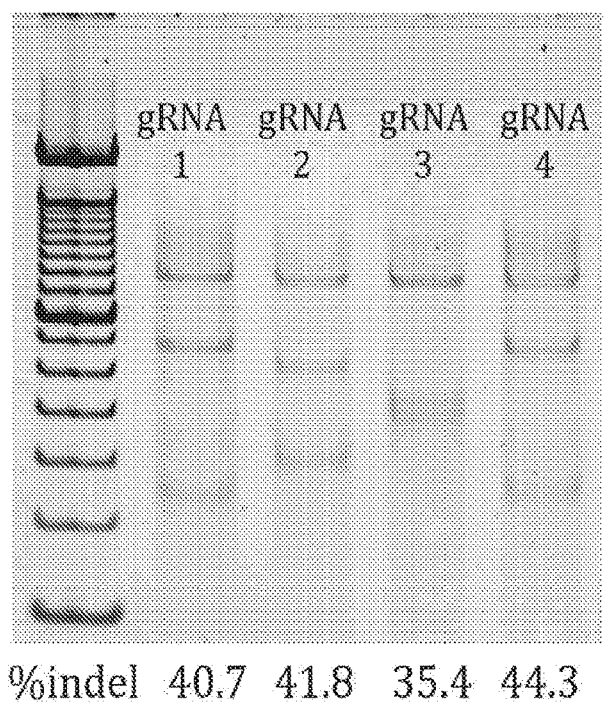
FIG. 9A is an image depicting SURVEYOR® assay testing targeting efficiency of guide RNA (gRNA) sequences within the dystrophin locus. The percentage of insertions or deletions is shown at the bottom of each lane.
Figure 9B:
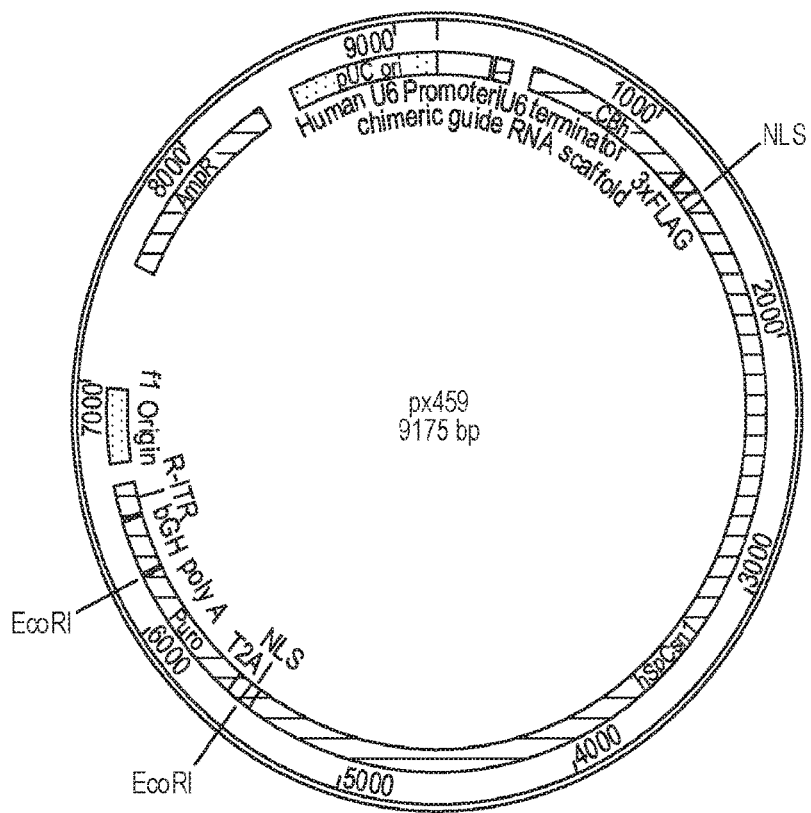
FIG. 9B is a schematic representation of the targeting plasmid containing guide sequence.

Forward and reverse single strand oligo deoxynucleotides (ssODN) were synthesized with Bbsl enzyme sites added at both ends (EUROFINS GENOMICS™, Huntsville, Ala.). The forward and reverse oligos were annealed, phosphorylated, and cloned into plasmid hSpCas9 (BB)-2A-Puro (px459, ADDGENE #48139) according to methods described previously (see Ran, F. A. et al., *Nat Protoc* 8, 2281-2308 (2013)) (see FIG. 9B). Ligation products were treated with PLASMID-SAFE™ ATP-dependent DNase (EPICENTRE®, Chicago, Ill.) before transforming into ONE SHOT® STBL3™ chemically competent *E. coli* (LIFE TECHNOLOGIES™). Integration of the plasmid was confirmed by Sanger sequencing (GENEWIZ™, Seattle, Wash.) using U6 primer.

Functional validations of the guide sequence were carried out by transfecting HEK293 cells with the aforementioned plasmids. Briefly, 293T cells were plated in 24-well plates at 130,000 cells/well in DMEM high glucose medium (LIFE TECHNOLOGIES™) with 10% fetal bovine serum (FBS). 800 ng of plasmid DNA was diluted with OPTI-MEM™

(LIFE TECHNOLOGIES™) and transfected into 293T cells with LIPOFECTAMINE® 2000 (LIFE TECHNOLOGIES™). Puromycin at 1.25 µg/ml was added to the medium starting at 1 day post transfection, and genomic DNA was harvested 3 days post transduction by DNAEASY™ BLOOD & TISSUE KIT (QIAGEN™, Valencia Calif.) according to the manufacturer's instruction. The DNA dystrophin locus was PCR amplified by PHUSION HIGH-FIDELITY HOT START II DNA POLYMERASE™ (THERMO SCIENTIFIC™, Waltham, Mass.) using primer set DMD-F: 5'-TGTAAAACGACGGCCAGTGGCCTC-TACAGAATCCTGGC-3' (SEQ ID NO:3) and DMD-R: 5'-CAGGAAACAGCTATGACAGGCCTC-CATGTAGTTCCTA-3' (SEQ ID NO:4). The PCR products from individual reactions were purified by a QIAQUICK™ PCR PURIFICATION KIT. SURVEYOR® assays were performed according to the manufacturer's instruction, and SURVEYOR® nuclease digestion products were electrophoresed on a 4-20% gradient polyacrylamide TBE gel, stained with SYBR® Gold dye diluted 1:10,000 in TBE buffer, and visualized in a CHEMIDOC™ imaging system (BIO-RAD™, Hercules, Calif.).

Example 3—Genome Targeting and Cell Cloning hSpCas9 (BB)-2A-Puro incorporated guide sequence 4 was chosen to transfect normal male iPSCs (UC 3-4) to generate a dystrophin knockout cell line. After being dissociated with VERSENE™ reagents (LIFE TECHNOLOGIES™), $3 \times 10^6$ of UC3-4 iPSCs were transfected using a NEON® TRANSFECTION SYSTEM (LIFE TECHNOLOGIES™) following the manufacturer's instruction. Cells were gently plated into 500 µl of MTESR™1 Medium (STEMCELL™ TECHNOLOGIES) with 10 µg/ml of ROCK inhibitor Y-26732 (SELLECK CHEMICALS™) in a well of a 24-well plate. Medium was refreshed every day, and 0.8 µg/ml puromycin selection was started 2 days post transduction for 48 hours. Surviving colonies were manually picked and passaged into a MATRIGEL™-coated 96-well plate for further expansion. Genomic DNA of individual colonies was extracted for PCR amplification of the targeted dystrophin region. Mutation of the dystrophin locus was confirmed by sequencing as described above.

Example 4—Testing for Dystrophin mRNA Using Real-Time Quantitative Polymerase Chain Reaction (gPCR)

TAQMAN® quantitative PCR was carried out using PCR probe sets (APPLIED BIOSYSTEMS®) amplifying different isoforms of the DMD. Total cellular mRNA was extracted from differentiated cardiomyocytes using RNEASY™ MINI KIT (QIAGEN™, Valencia Calif.). cDNA was reverse-transcribed from 500 ng total RNA with 200 units of SUPERSCRIPT® II REVERSE TRANSCRIPTASE (LIFE TECHNOLOGIES™) with 1 µl of Oligo(dT)12-15 at 500 µg/ml, according to the manufacturer's instructions. cDNA was diluted 5-fold with DI water. 4 µl of diluted cDNA was included in a 20 µl volume reaction with 1 µl of 20× TAQMAN® GENE EXPRESSION ASSAY, 10 µl of 2× TAQMAN® GENE EXPRESSION MASTER MIX in 96-well format. The PCR reaction was carried out with 7900HT FAST REAL-TIME PCR SYSTEM (LIFE TECHNOLOGIES™). All data was analyzed using SDS software v2.3 (LIFE TECHNOLOGIES™). Relative quantitation of target gene expression was normalized against GAPDH and compared with normal cardiomyocytes.

Example 5—Immunostaining for Dystrophin Protein

Cardiomyocytes were plated onto MATRIGEL™-coated coverslips. Attached cells were fixed with 4% paraformaldehyde for 10 minutes and permeabilized with 0.1% TRITON™× in PBS for 5 minutes. After blocking with DAKO™ serum free protein block, samples were probed with primary antibody against dystrophin (ABCAM, Cambridge Mass.) and sarcomeric α-actinin (1:200, LIFE TECHNOLOGIES™) overnight at 4° C. The next day, samples were probed with FITC-anti rabbit IgG and TXRED® anti mouse IgG (both at 1:200). Nuclei were counter stained with DAPI and mounted onto glass slides with ANTIFADE™ GOLD mounting medium (LIFE TECHNOLOGIES™). All images were captured with NIKON® A1 confocal microscope and processed with NIKON® ELEMENTS advanced research analysis software (Version 3.2 64 bit).

Example 6—Western Blots

Western blots were conducted according to the method described previously, with modification (see Guan, X. et al., Stem Cell Res 12, 467-480 (2014)). Briefly, differentiated cardiomyocytes were lysed by RIPA buffer (THERMO SCIENTIFIC™) with PIERCE™ protein inhibitor (LIFE TECHNOLOGIES™), and protein concentrations were determined by DC™ PROTEIN ASSAY reagents (BIO-RAD™). 10 µg of cell lysates were loaded for electrophoresis. Dys1, Dys2, and Dys3 monoclonal antibodies (1:100, 1:50, and 1:50 LEICA™) were used as the primary antibodies to probe dystrophin (see Table 1). A mouse monoclonal antibody to cardiac myosin heavy chain (ab15, 1:1000, ABCAM) was used as a protein loading control. ALEXA FLUOR® 488 goat anti mouse IgG1 and ALEXA FLUOR® 549 Goat anti mouse IgG2a (LIFE TECHNOLOGIES™, 1:1000) were used as secondary antibodies for multiplexing. Blots were imaged by a CHEMIDOC™ MP imaging system (BIO-RAD™, Hercules Calif.).

TABLE 1

| Antibody | AA Sequence | Corresponding mRNA |
|---|---|---|
| Dys1 | 1181-1388 | Exon 26-30 |
| Dys2 | 3668-3684 | Exon 77-79 |
| Dys3 | 321-494 | Exon 10-12 |

Example 7—Mitochondrial Permeability Transition Pore (mPTP) Opening Time

Cardiomyocytes were loaded with tetramethylrhodamine ethyl ester (TMRE), a fluorescent indicator that accumulates in the mitochondria proportionally to the $\Delta\Psi m$, and exposed to controlled and narrowly-focused laser-induced oxidative stress until mPTP opening occurred (see Pravdic, D. et al., Anesthesiology 111, 267-274 (2009)). To ensure equal delivery of oxidative stress among experimental groups, laser excitation settings remained consistent within the experimental groups. Mitochondrial PTP opening was detected by a decrease in TMRE fluorescence, which indicates loss of $\Delta\Psi m$. Arbitrary mPTP opening time was determined as the

Example 8—Hypotonic Stress Experiment ELISA

Differentiated cardiomyocytes were seeded into a 96-well plate at 50,000 cells/well for 7 days. Hypotonic solutions with various osmolarities were reconstituted by mixing DPBS with ddH$_2$O (LIFE TECHNOLOGIES™) Cardiomyocytes were treated with hypotonic solutions for 30 minutes at room temperature. Supernatants were collected to assay creatine kinase MB (CKMB) concentration by ELISA (MESO SCALE DISCOVERY™). All data were normalized against total cellular CKMB, determined by directly lysing control wells without stress.

Example 9—Hypotonic Stress Experiment with FM 1-43 Live Imaging

Differentiated cardiomyocytes were seeded into NUNC™ 8-well chambered coverglass (THERMO SCIENTIFIC™, Waltham Mass.) at 100,000 cells/well for attachment. FM 1-43 (LIFE TECHNOLOGIES™) was diluted in DPBS and ddH$_2$O at 2.5 µM. Cardiomyocytes were incubated with 150 µl of FM 1-43 in DPBS for 5 minutes at room temperature to stain membrane. Time-lapse image sequences were collected with a NIKON® A1 confocal microscope (NIKON® INSTRUMENT INC., Melville, N.Y.) at the frequency of 1 frame/5 seconds for 20 minutes. 600 µl of ddH$_2$O containing 2.5 µM FM 1-43 were injected into the well after 60 seconds to adjust the final osmolarity to 20% of normal osmolarity.

All image sequences were analyzed with IMAGEJ (see Schneider, C. A. et al., *Nat Methods* 9, 671-675 (2012)) and interpreted in a blinded fashion. Background was calculated as the average of the first 13 images within every sequence, corresponding to the baseline fluorescence signal before stress in hypotonic solution, and was subsequently subtracted for further processing. Membrane damaged cells were recognized with intracellular FM 1-43 accumulation. Numbers of total cells and membrane-damaged cells were separately counted at both 65 s and 1200 s using the Cell Counter plugin of IMAGEJ. Percentage of membrane damaged cells was calculated as (Number of FM 1-43 positive$_{1200s}$–Number of FM 1-43 Positive$_{65s}$)/Total cell number.

The fluorescence intensity of image sequence was extracted with the Time Analyzer plugin and filtered by a Gaussian 3D filter of size 4.0 in all directions. Filtered data was analyzed in EXCEL™ and plotted by GRAPHPAD PRISM™ 6 (GRAPHPAD SOFTWARE™, San Diego, Calif.).

Example 10—High-Throughput Screening

Fourteen days post differentiation, cardiomyocytes were dissociated into single cell suspension by incubating for 5 minutes with TRYPLE™ (LIFE TECHNOLOGIES™) and plated at 10,000 cells/well on opaque-bottom 384-well plates (NUNC™) pre-coated with 1 mg/mL MATRIGEL™ (CORNING®) for 1 hour at 37° C. To allow cardiomyocytes to mature, cells were cultured on the 384-well plates for 16 days, with media being exchanged every 72 hours. After 15 days, compounds dissolved in DMSO were distributed to the plates using the CYBI®-WELL VARIO 384/25 liquid handler (CYBIO™, Germany) to achieve a concentration of $10^{-8}$, $10^{-7}$, $10^{-6}$, $10^{-5}$ M in duplicate. After 18 hours of incubation, medium was aspirated and pure water was injected to reach the 12.5% normal osmolarity using BIOTEK® EL406 WASHER DISPENSER (BIOTEK®, Winooski, Vt.). After 30 minutes of incubation, supernatants were removed and plates were assayed by adding CELLTITER-GLO® (PROMEGA™) according to the manufacturer's instruction. After 5 minutes, the luminescence was measured using ENVISION™ multilable reader) (PERKINELMER®). All data were processed and visualized by TIBCO® SPOTFIRE® (TIBCO® SPOTFIRE®, Boston, Mass.). Percentage viability was calculated by comparing signal from each well to the average of control wells treated with DMSO alone (32 control wells/plate). Taking consideration of Z score ranking (>3), standard deviation of replicates, and escalating dose-ranging response, 39 hits were identified from 2,000 input compounds (~2% hit rate) (see Table 3 below).

Example 11—Generation of an Isogenic Dystrophin-Null iPSC Line

A human iPSC line harboring a single base pair deletion (c.263delG) results in premature termination of dystrophin translation. To create an isogenic dystrophin-null iPSC line, the dystrophin locus of a normal male iPSC line (see Guan, X. et al., *Stem Cell Res* 12, 467-480 (2014)) was targeted by CRISPR-Cas9 enzyme around the N-terminus coding region within exon 1 of Dp427m (see FIG. 1A), the predominant dystrophin isoform of heart muscle. The targeting efficiency of guide RNA (gRNA) sequences was tested in HEK293T cells. SURVEYOR® assay confirmed all sequences precisely targeted the expected genomic region, and the guide yielding the highest cutting efficiency (44.3%), gRNA 4, was chosen for dystrophin locus modification (see FIG. 9A).

Figure 1B:
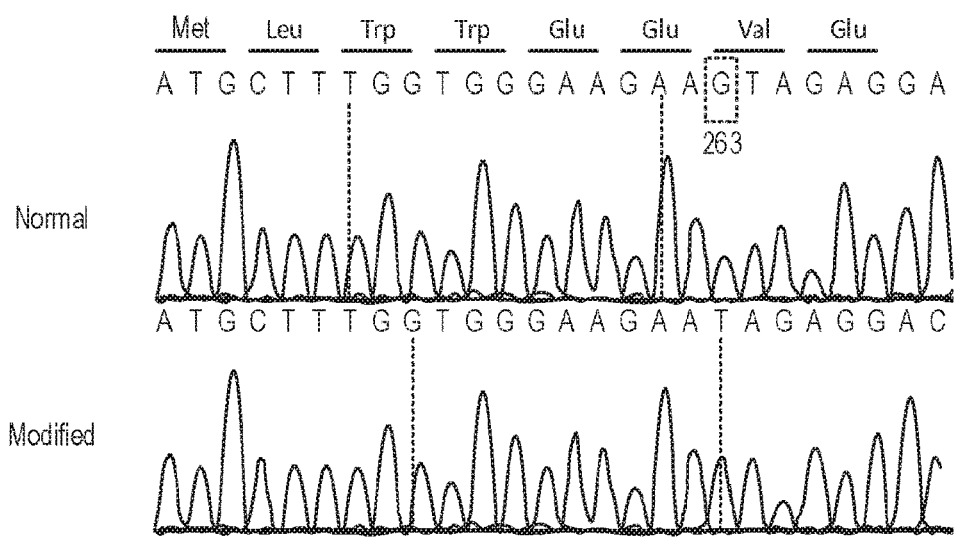
FIG. 1B is a Sanger sequencing trace illustrating the location around the modified region in both normal and modified iPSC lines. The translated dystrophin N-terminus protein is shown at the top.
Figure 1C:
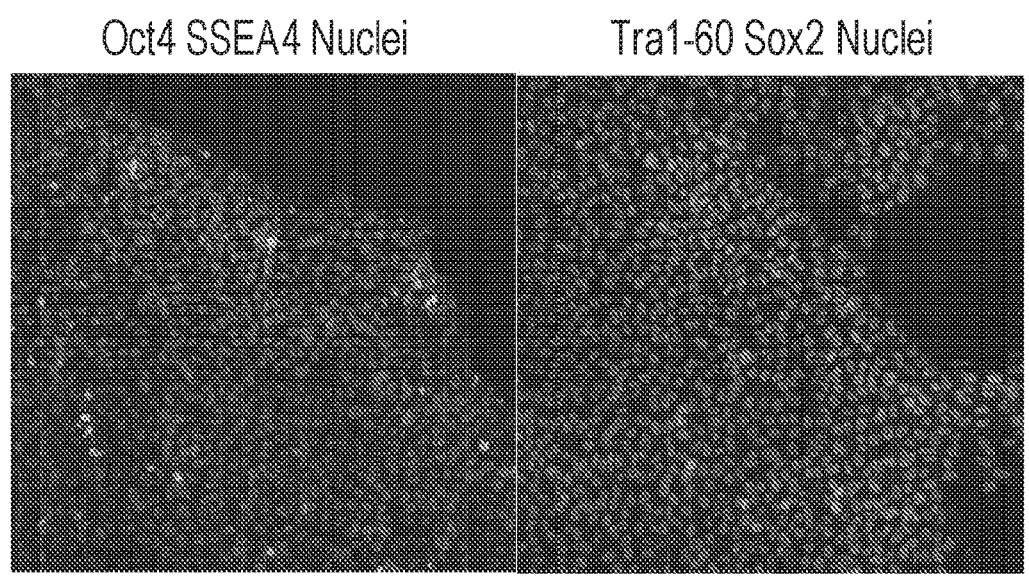
FIG. 1C depicts immunocytochemistry staining of Oct4, SSEA4, Sox2, and Tra-1-60, in typical colonies of c.263delG. The immunocytochemistry staining indicates the dystrophin-mutant line, c.263delG, expresses pluripotent markers after genome editing.
Figure 1D:
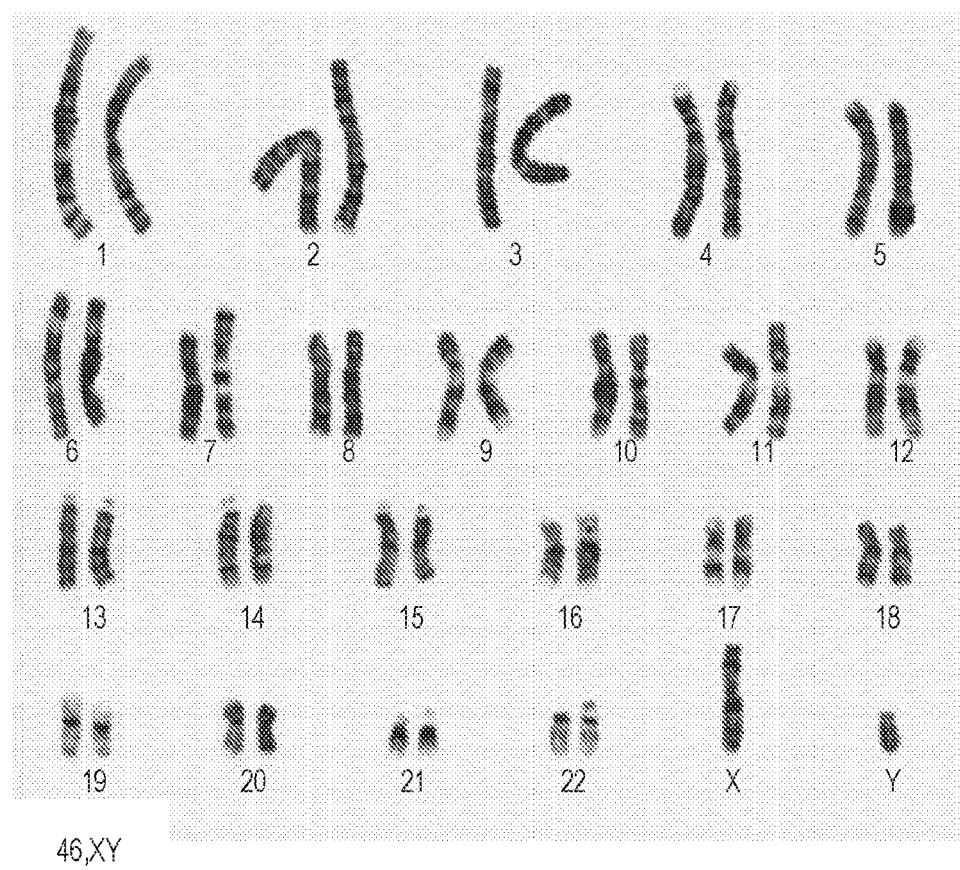
FIG. 1D depicts a G-banding karyogram of the dystrophin-mutant iPSC line, which indicates a normal human karyotype.

Subsequently, gRNA 4 was cloned into the wild-type CRISPR-Cas9 plasmid hSpCas9 (BB)-2A-Puro(px459) to create a double strand break in normal iPSCs. Those iPSC clones that survived puromycin selection were expanded and sequenced to identify 2 out of 20 clones containing insertion/deletions (indels) at the targeted region. One clone revealed a deletion of guanine 263 (c.263delG) (see FIG. 1B), which shifts the reading frame to prematurely terminate dystrophin translation. The dystrophin-mutant line, c.263delG, maintains normal stem cell morphology and expresses pluripotency-related markers, including Oct4, SSEA4, Tra-1-60, and Sox2 (see FIG. 1C) and retains a normal karyotype (see FIG. 1D).

Example 12—Measurement of Dystrophin Expression

Figure 2D:
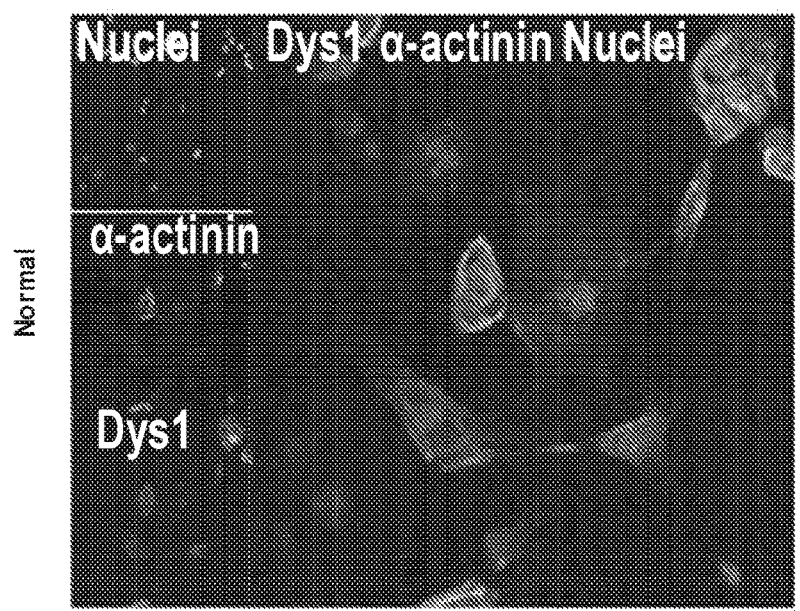
FIG. 2D shows two micrographs indicating the presence of dystrophin only in normal cardiomyocytes but not in mutant cells.
Figure 2D:
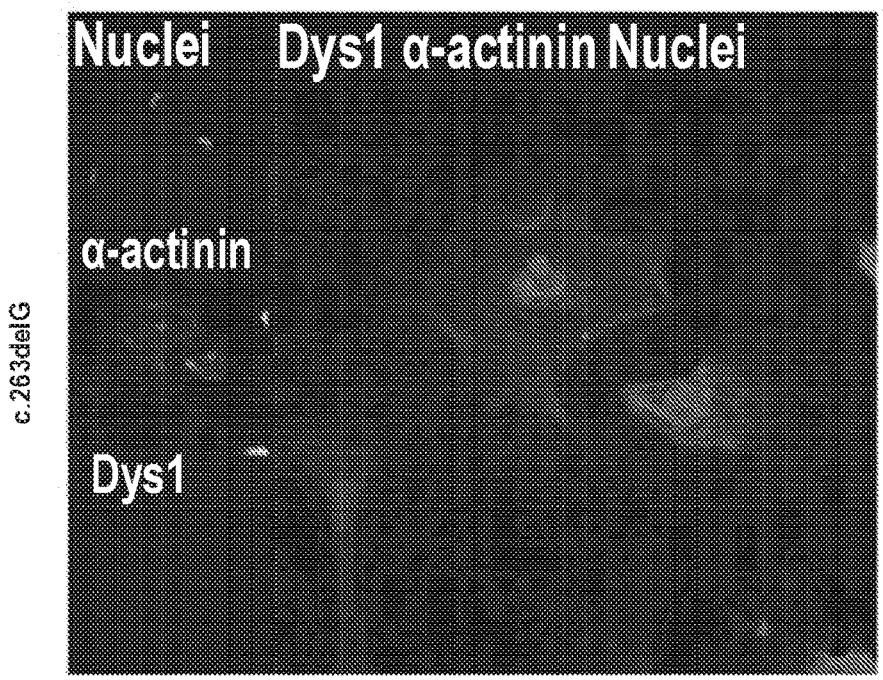

Cardiomyocytes derived from c.263delG mutant human iPSCs fail to express dystrophin. To measure dystrophin expression at the mRNA level, differentiated human cardiomyocytes from normal, DMD patient, and CRISPR-Cas9-engineered iPSC lines were evaluated by RT-PCR. Three pairs of PCR probes were employed to detect mRNA transcripts at different regions across the cDNA sequence (see FIG. 2A and Table 2): Probe 1 specifically detects Dp427m, the predominant isoform of the heart; Probe 2 targets the central rod domain, shared by isoform Dp427 and Dp270; and Probe 3 recognizes the C terminus shared by all isoforms Dp427, Dp270, and Dp71. While the DMD patient cardiomyocytes (Δexon 50) demonstrated overall transcripts reduction, mutant (c.263delG) cardiomyocytes exhibited a different expression profile. Compared to normal cardiomyocytes, Probe 1 failed to detect any mRNA transcript, while Probes 2 and 3 detected comparable or even higher transcript levels (see FIG. 2C). The presence of dystrophin protein was further assayed by immunocytochemistry and western blots. Immunostaining revealed that α-actinin-positive normal cardiomyocytes stained positive for dystrophin, while mutant cardiomyocytes c.263delG were negative (see FIG. 2D). The absence of dystrophin protein was further corroborated by western blot; three antibodies against different epitopes failed to detect the 427 kDa dystrophin protein in mutant cardiomyocytes. These results indicate a dystrophin-null cardiac phenotype was created by CRISPR-Cas9 methodology.

TABLE 2

| Probe | Exons | Protein |
|---|---|---|
| 1 | Exon 1-2 | Dp427m specific N terminus |
| 2 | Exon 47-48 | Central rod domain |
| 3 | Exon 75-76 | C-terminus (Common) |

Example 13—Dystrophin-Null Cardiomyocytes Display Abnormal Calcium Handling

Figure 3A:
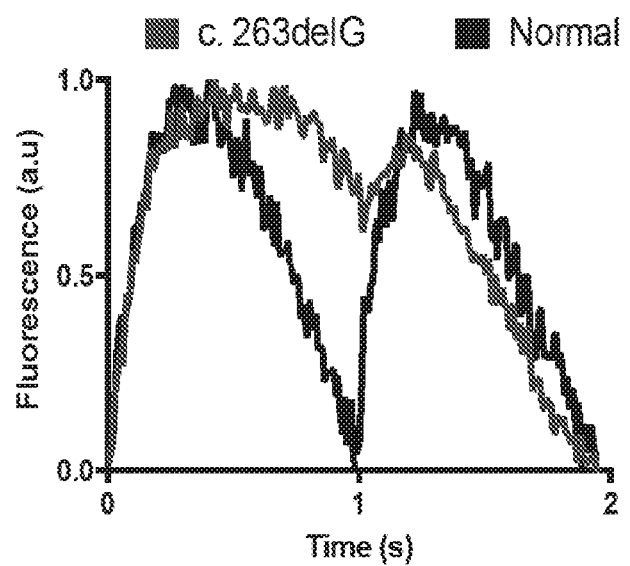
FIG. 3A is a representative tracing of 1 Hz field-stimulated intracellular calcium transients in both normal and mutant cardiomyocytes (c.263delG).
Figure 3B:
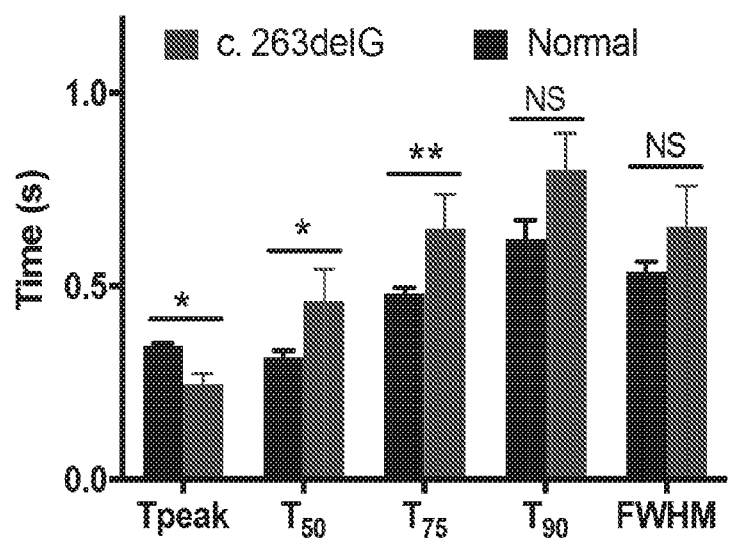
FIG. 3B is a graph summarizing Time to Peak (Tpeak), $T_{50}$, $T_{75}$, $T_{90}$, and FWHM measurements of normal (n=8) and c.263delG mutant cardiomyocytes (n=9), demonstrating calcium handling differences between the isogenic pair. This finding suggests that dystrophin-null cardiomyocytes manifested shorter time to peak but prolonged calcium reuptake.

To determine whether dystrophin deficiency directly results in abnormal calcium handling in human cardiomyocytes, calcium transients were measured and compared between normal and isogenic c.263delG cardiomyocytes. External 1 Hz pacing failed to drive several mutant cardiomyocytes, while normal control cells all responded to the stimulation (see FIG. 3A). The mutant demonstrated a faster time to Peak (Tpeak). Temporal parameters $T_{50}$ and $T_{75}$ were significantly higher in mutant cells than in normal control ($T_{50}$: 0.31±0.05 s vs. 0.46±0.25 s; $T_{75}$: 0.48±0.04 s vs. 0.65±0.26 s, normal and c.263delG, respectively), while $T_{90}$ and full width at half maximum (FWHM) were not significantly different ($T_{90}$: 0.62±0.14 s vs. 0.8±0.28 s; FWHM: 0.54±0.07 s vs. 0.65±0.32 s, normal and c.263delG, respectively) (see FIG. 3B).

Example 14—Dystrophin Deficiency and Opening Kinetics of mPTP

Figure 4A:
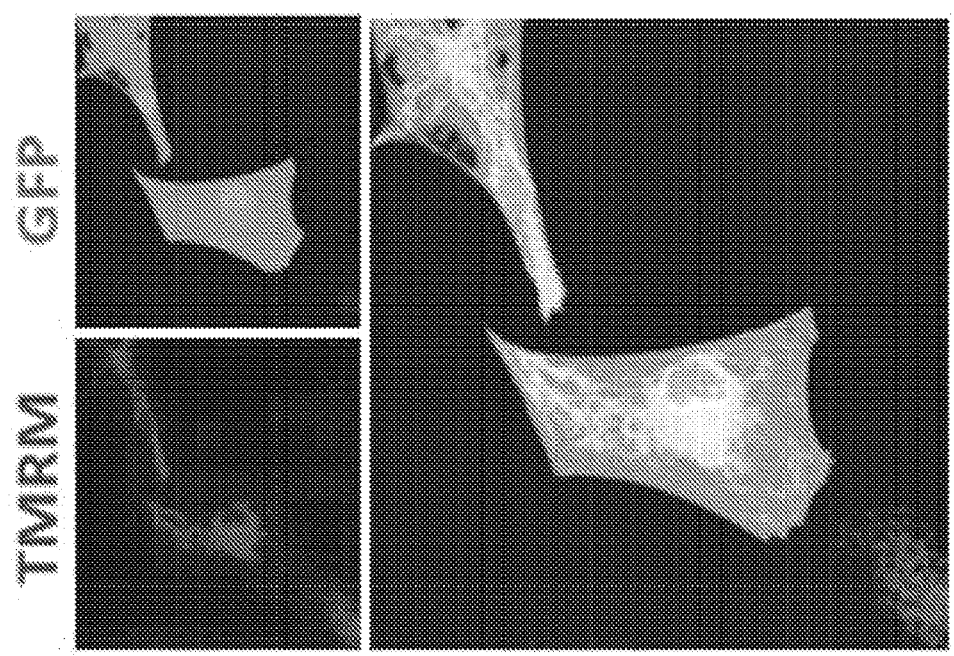
FIG. 4A depicts cNCX-GFP labeled cardiomyocytes stained with mitochondria dye TMRM.
Figure 4B:
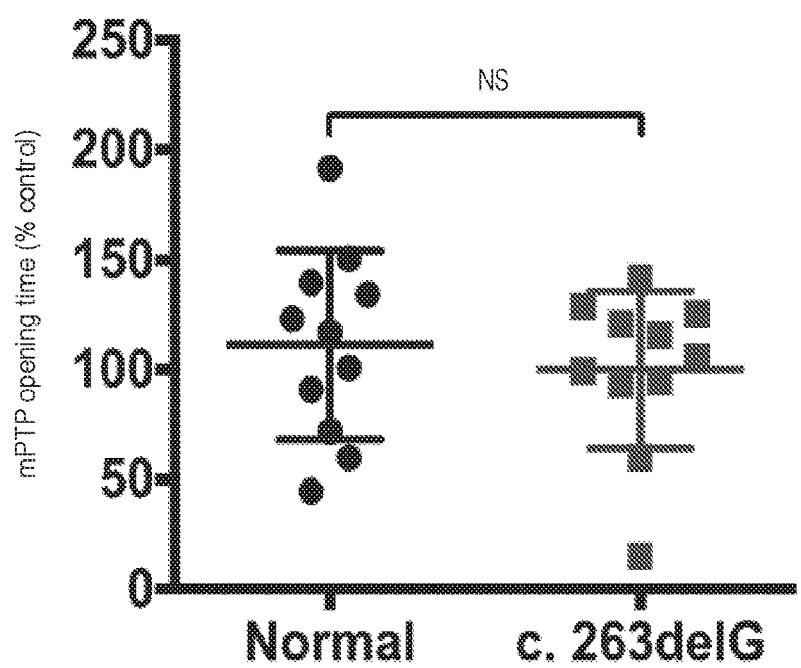
FIG. 4B is a graph depicting the mPTP opening time, determined as the average time of 50% TMRE fluorescence drop in relation to normal control (n=15 for normal, n=22 for c.263delG).

Dystrophin deficiency does not alter opening kinetics of the mPTP. To test whether dystrophin deficiency leads to accelerated mPTP opening, opening kinetics of the MPT pore were measured in dystrophin-null (c.263delG) and dystrophin-replete (normal) cardiomyocytes. cNCX-GFP labeled cardiomyocytes were pre-loaded with mitochondria dye TMRM (see FIG. 4A). Results indicated comparable mPTP opening time between normal and c.263delG cardiomyocytes ($T_{50}$: 102.9±35.5 s vs. 117.3±37.8, normal and c.263delG, respectively) (see FIG. 4B).

Example 15—Dystrophin Deficiency and Osmotic Stress

Figure 5A:
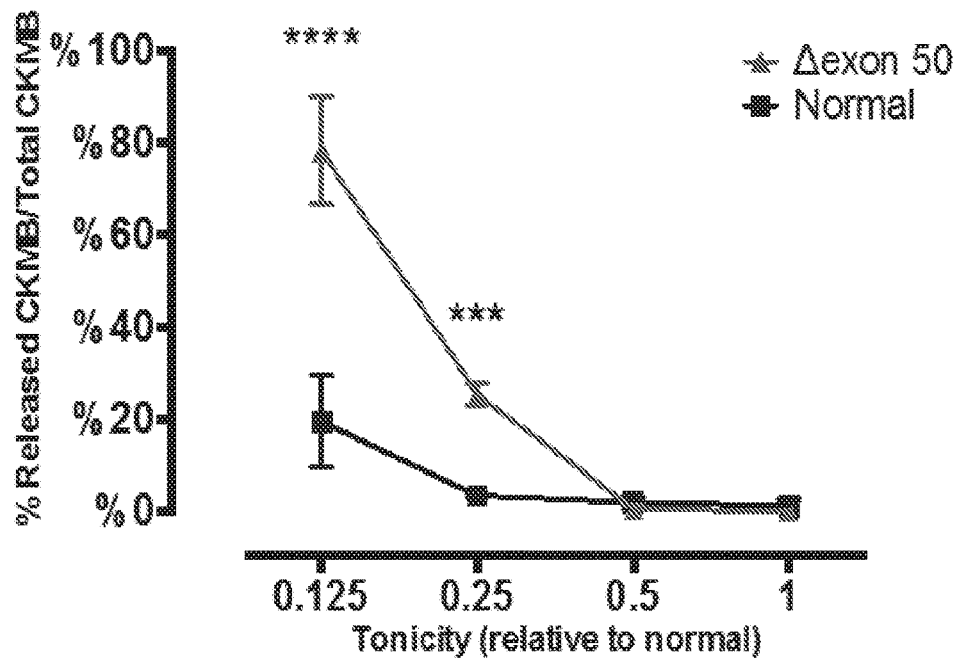
FIG. 5A is a graph depicting normal cardiomyocytes and DMD patient cardiomyocytes (Δexon 50).
Figure 5B:
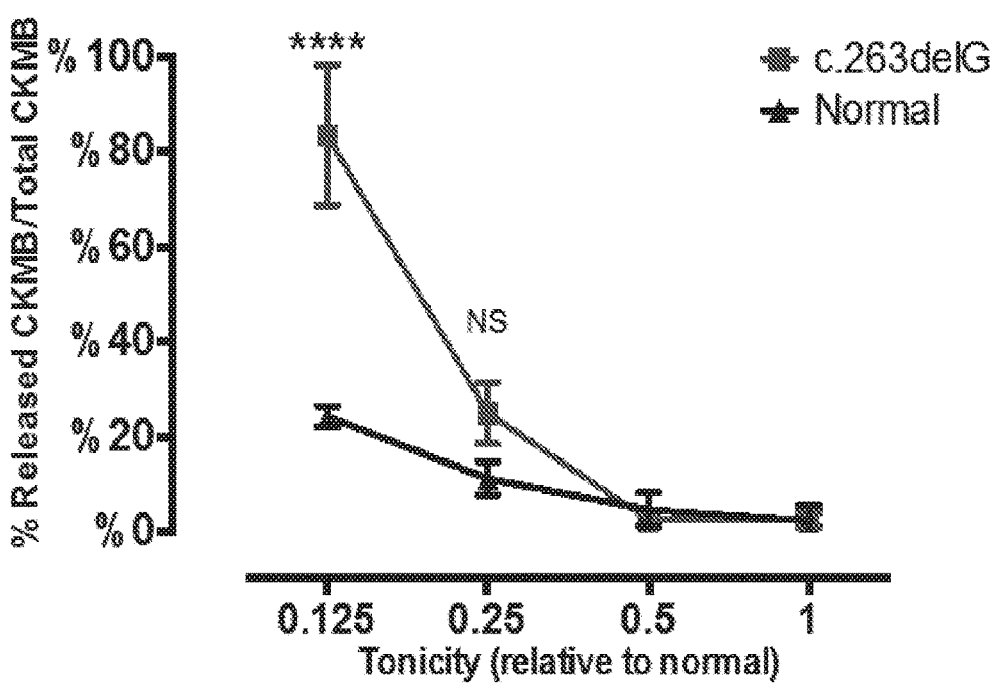
FIG. 5B is a graph depicting normal and engineered cardiomyocyte line (c.263delG).

Dystrophin deficiency renders human cardiomyocytes abnormally vulnerable to osmotic stress. To directly test whether the loss of dystrophin renders human cardiomyocytes abnormally vulnerable to mechanical stress, cultured cells were subjected to an established test of osmotic fragility. Human cardiomyocytes were challenged by hypotonic saline incubation to stretch the membrane. Liberation of intracellular creatine kinase MB (CKMB), a cardiac injury marker, was measured in the post-stretched supernatants. Both normal and DMD cardiomyocytes released CKMB. However, DMD patient cardiomyocytes (Δexon 50) released significantly higher CKMB at 25% and 12.5% of normal osmolality (25% osmolarity: 3.4±0.4% vs. 25.5±2.4%, 12.5% osmolarity: 19.6±10% vs. 78.4±11.6%, normal vs. Δexon 50) (see FIG. 5A). Similar to DMD patient cardiomyocytes, engineered mutant c.263delG cardiomyocytes revealed a similar CKMB release profile (25% osmolarity: 11.3±1.8% vs. 25±3.8%; 12.5% osmolarity: 24.2±1.1% vs. 83.4±8.5%, normal vs. c.263delG) (see FIG. 5B). Taken together, these data show that dystrophin deficiency directly results in increased cell damage in human cardiomyocytes.

To further examine the dynamic alteration of membrane barrier function, cardiomyocytes were subjected to time-lapse examination in the presence of a lipophilic fluorescent indicator, FM 1-43, under hypotonic conditions. FM 1-43 can only gain access to the cytoplasm through sarcolemma micro-ruptures. As a result, intracellular accumulation of FM 1-43 is a good indicator of the breach of membrane integrity (see Idone, V. et al., *J Cell Biol* 180, 905-914 (2008)). To gain a finer temporal resolution, fluorescence intensity of the whole image was assessed as a surrogate indicator of the loss of membrane integrity. On the basis of fluorescence output, c.263delG mutant cardiomyocytes demonstrated an initial faster dye accumulation from 80 s to 110 s (initial 30 s of hypotonic stress) (see FIGS. 5C and 5D). After 20 minutes of 20% hypotonic stress, c.263delG mutant cells demonstrated higher percentages of cells with intracellular dye accumulation than isogenic normal controls (65.8±3.8% vs. 40.8±5.7%, p=0.014) (see FIG. 5E). These results indicate that dystrophin deficient cells demonstrated early-phase membrane integrity compromise after exposure to stress.

Example 16—Generation of a High-Throughput Format for Drug Discovery

To test whether hypotonic stress diminishes intracellular ATP (a widely used assay of cell viability in high-throughput screens), experiments were conducted to compare effects of hypotonic stress on CKMB release and ATP content. Following 30 minutes of hypotonic stress, dystrophin deficient cells demonstrated smaller ATP content compared to isogenic normal controls under all tested conditions (see FIG. 6C). Moreover, an inverse correlation existed between CKMB release and ATP content in both the engineered mutant c.263delG (see FIG. 6A, r=−0.9) and normal (see FIG. 6B, r=−0.8) cardiomyocytes. These data indicate that a widely used cell viability assay measuring intracellular ATP could be a useful readout to search for agents that enhance survival of dystrophin deficient cells.

Figures 7A, 7B:
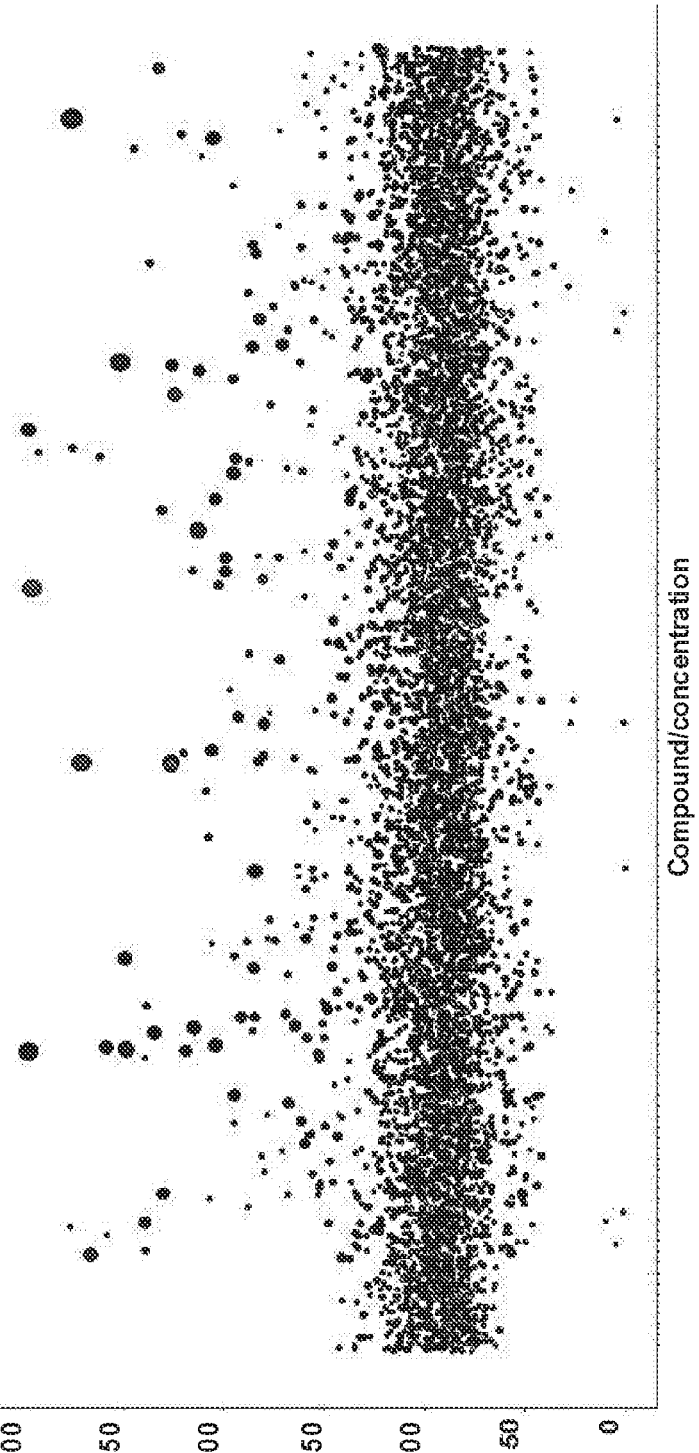
FIG. 7A is a schematic illustration of screening workflow according to an embodiment of the present disclosure.
FIG. 7B depicts the results from the primary screen (2,000 compounds at 4 concentrations total 8,000 data points). The results are plotted as the percentage of overall average intracellular ATP.

After optimizing the phenotype assay, a medium-throughput, semi-automated screen was conducted (see FIG. 7A) with a small library including 2,000 diverse molecules with annotated mechanisms of action. Overall, the Z prime of the assay was 0.71. The 8,000 data points were plotted against the percentage of cell viability (see FIG. 7B) and were re-ranked based on the Z score (see FIG. 8). Taking consideration of Z score ranking (>3), standard deviation of replicates and escalating dose-ranging response, 39 hits were identified from 2,000 input compounds (~2% hit rate) (see Table 3).

TABLE 3

Primary Screening Hits

| Compound | Average of % viability | Z score | Mechanism of action |
| --- | --- | --- | --- |
| ACEPROMAZINE MALEATE | 239.1 ± 38.37 | 6.57 | Sedative |
| ACYCLOVIR | 258.33 ± 14.16 | 7.44 | Antiviral |
| AKLOMIDE | 276.60 ± 12.37 | 8.26 | Antiprotozoal, Coccidiostat |
| ALTRETAMINE | 188.22 ± 2.87 | 4.27 | Antineoplastic |
| AMINOHIPPURIC ACID | 207.49 ± 7.09 | 5.14 | Renal function diagnosis |
| AMIODARONE HYDROCHLORIDE | 168.14 ± 8.45 | 3.37 | Adrenergic agonist, coronary vasodilator, calcium channel blocker |
| ANTIMYCIN A | 180.04 ± 1.89 | 3.90 | Antifungal, antiviral, interferes in cytochrome oxidation |
| ASCORBIC ACID | 181.48 ± 23.68 | 3.97 | Antiscorbutic, antiviral |
| ATENOLOL | 171.27 ± 1.77 | 3.51 | Beta adrenergic blocker |
| BENZALKONIUM CHLORIDE | 194.64 ± 23.10 | 4.56 | Anti-infective (topical) |
| BEPRIDIL HYDROCHLORIDE | 178.65 ± 3.48 | 3.84 | Antiarrhythmic |
| BIOTIN | 315.95 ± 51.89 | 10.04 | Vitamin B complex |
| CANTHARIDIN | 239.59 ± 14.65 | 6.59 | Blister agent (terpenoid) |
| CEFDINIR | 185.70 ± 45.76 | 4.16 | Antibacterial |
| CHLORCYCLIZINE HYDROCHLORIDE | 238.84 ± 35.23 | 6.56 | H1 antihistamine |
| CINCHOPHEN | 168.44 ± 44.63 | 3.38 | Analgesic, antipyretic, anti-inflammatory |
| CLOPIDOGREL SULFATE | 194.84 ± 50.3 | 4.57 | Platelet aggregation inhibitor |
| CORTISONE ACETATE | 205.92 ± 12.32 | 5.07 | Glucocorticoid |
| COTININE | 188.79 ± 56.0 | 4.30 | Antidepressant |
| CROTAMITON | 178.25 ± 27.22 | 3.82 | Antipruritic, Scabicide |
| DACARBAZINE | 177.63 ± 45.35 | 3.79 | Antineoplastic |
| DOXORUBICIN | 207.98 ± 34.29 | 5.16 | Antineoplastic |
| ESTROPIPATE | 208.65 ± 30.77 | 5.19 | Estrogen |
| GITOXIGENIN DIACETATE | 177.20 ± 1.17 | 3.77 | Cardiac glycoside |
| HALOPERIDOL | 197.30 ± 19.03 | 4.68 | Antidyskinetic, antipsychotic |
| HYDROXYUREA | 187.65 ± 49.61 | 4.25 | Antineoplastic, inhibits ribonucleoside diphosphate reductase |
| MEBHYDROLIN NAPHTHALENE SULFONATE | 172.81 ± 39.86 | 3.58 | H1 antihistamine |
| NAPROXOL | 168.76 ± 2.61 | 3.39 | Anti-inflammatory, analgesic, antipyretic |
| NICOTINYL ALCOHOL TARTRATE | 262.12 ± 57.89 | 7.61 | Vasodilator |
| NIMODIPINE | 292.38 ± 56.17 | 8.97 | Calcium channel blocker, vasodilator |
| NITRENDIPINE | 275.48 ± 52.16 | 8.21 | Calcium channel blocker, vasodilator |
| OXYPHENBUTAZONE | 176.96 ± 42.53 | 3.76 | Anti-inflammatory |
| PODOFILOX | 168.46 ± 28.98 | 3.38 | Antineoplastic, inhibits microtubule assembly, and human DNA topoisomerase II; antimitotic agent |
| PROGLUMIDE | 175.69 ± 50.35 | 3.71 | Anticholinergic |
| PUROMYCIN HYDROCHLORIDE | 187.84 ± 39.68 | 4.25 | Antineoplastic, antiprotozoal |
| RETINYL PALMITATE | 236.79 ± 46.63 | 6.46 | Provitamin, antixerophthalmic |
| SELAMECTIN | 172.91 ± 25.29 | 3.58 | Antiparasitic, antimite |
| SULFADOXINE | 195.32 ± 23.52 | 4.59 | Antibacterial |
| TERFENADINE | 211.28 ± 22.46 | 5.31 | H1 antihistamine, nonsedating, |
| TILORONE | 172.53 ± 15.79 | 3.56 | Antiviral |

Certain embodiments of this disclosure are described herein, including the best mode known to the inventors for carrying out the disclosure. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications is individually incorporated herein by reference in its entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

It will be apparent to those having skill in the art that many changes may be made to the details of the above-described embodiments without departing from the underlying principles of the disclosure. The scope of the present invention should, therefore, be determined only by the following claims.

The invention claimed is:

1. A method of screening an agent for an effect on membrane barrier function of a cardiomyocyte population, the method comprising:
 (a) obtaining a cardiomyocyte population differentiated from a dystrophin knockout induced pluripotent stem cell (iPSC) line derived by targeted mutagenesis of the dystrophin locus in a normal iPSC line bearing a normal karyotype, wherein the cardiomyocyte population comprises a deletion of guanine 263 (c.263delG) in the Dp427m dystrophin isoform;
 (b) contacting the cardiomyocyte population in (a) with an agent; and
 (c) determining an effect of the agent on membrane barrier function in the cardiomyocyte population.

2. A method of screening an agent for an effect on membrane barrier function in a dystrophin knockout cardiomyocyte population, the method comprising:
 (a) obtaining a dystrophin knockout induced pluripotent stem cell (iPSC) population derived by targeted mutagenesis of the dystrophin locus in a normal iPSC line bearing a normal karyotype;
 (b) differentiating the dystrophin knockout iPSC population to form a dystrophin knockout cardiomyocyte population;
 (c) contacting the dystrophin knockout cardiomyocyte population with an agent; and determining an effect of the agent on membrane barrier function in the dystrophin knockout cardiomyocyte population.

3. The method of claim 2, wherein the dystrophin knockout iPSC population comprises a deletion of guanine 263 (c.263delG) in the Dp427m dystrophin isoform.

4. The method of claim 2, wherein the dystrophin knockout iPSC population expresses at least one of Oct4, SSEA4, Tra-1-60, and Sox2.

5. The method of claim 2, wherein the dystrophin knockout iPSC population expresses Oct4, SSEA4, Tra-1-60, and Sox2.

6. The method of claim 2, wherein:
 the dystrophin knockout cardiomyocyte population has one or more characteristics of a dystrophin deficient cardiomyopathy, and
 the one or more characteristics are selected from at least one of a decrease of membrane barrier function, slower calcium reuptake, expression of creatine kinase MB (CKMB), expression of troponin I, expression of troponin T, and susceptibility to mitochondria permeability transition pore (mPTP) opening.

7. The method of claim 2, further comprising:
 contacting the dystrophin knockout cardiomyocyte population with a hypotonic solution,
 wherein the determining an effect of the agent on membrane barrier function in the dystrophin knockout cardiomyocyte population comprises conducting a cell viability assay.

8. The method of claim 7, wherein the cell viability assay comprises quantification of ATP in the dystrophin knockout cardiomyocyte population.

9. The method of claim 2, wherein the dystrophin knockout cardiomyocyte population is human.

10. The method of claim 2, wherein the method is a high-throughput method.

11. The method of claim 2, wherein the agent is a drug.

* * * * *